(12) United States Patent
Xia et al.

(10) Patent No.: US 11,597,931 B2
(45) Date of Patent: Mar. 7, 2023

(54) READ THROUGH OF TRUNCATED PROTEINS IN PREMATURE TERMINATION CODON DISEASES USING AN OPTIMIZED GENETIC CODON EXPANSION SYSTEM

(71) Applicant: PEKING UNIVERSITY, Beijing (CN)

(72) Inventors: Qing Xia, Beijing (CN); Qi Yang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 61 days.

(21) Appl. No.: 16/987,050

(22) Filed: Aug. 6, 2020

(65) Prior Publication Data

US 2021/0024935 A1  Jan. 28, 2021

Related U.S. Application Data

(62) Division of application No. 16/083,766, filed as application No. PCT/CN2017/075577 on Mar. 3, 2017, now abandoned.

(30) Foreign Application Priority Data

Mar. 10, 2016  (CN) .......................... 201610134657.6

(51) Int. Cl.
| | | |
|---|---|---|
| C12N 15/113 | (2010.01) | |
| C12N 15/11 | (2006.01) | |
| C12N 15/67 | (2006.01) | |
| G01N 33/68 | (2006.01) | |

(52) U.S. Cl.
CPC .......... *C12N 15/1135* (2013.01); *C12N 15/11* (2013.01); *C12N 15/111* (2013.01); *C12N 15/67* (2013.01); *G01N 33/68* (2013.01); *C12N 2310/10* (2013.01); *C12N 2310/333* (2013.01); *C12N 2310/334* (2013.01); *C12N 2310/335* (2013.01)

(58) Field of Classification Search
CPC ........ C12N 15/11; C12N 15/111; C12N 15/67
See application file for complete search history.

(56) References Cited

U.S. PATENT DOCUMENTS

2010/0160416 A1  6/2010 Charo et al.

FOREIGN PATENT DOCUMENTS

| CN | 102504022 A | 6/2012 |
| WO | WO-2015/100277 A2 | 7/2015 |

OTHER PUBLICATIONS

Zheng et al (Nucl. Acids Res. 43(11): e73, 2015, 12 pages) (Year: 2015).*
Juan-Mateu et al (PLoS ONE 10(8): e0135189) (Year: 2015).*
Meregalli et al (BMC Medical Genetics (2016) 17:55, 6 pages) (Year: 2016).*
Bladen et al. (Human Mutation, 36(4): 395-402, 2015) (Year: 2015).*
Http://umd.be/TREAT_DMD/4DACTION/WS_T_AA_complet, retrieved on Jan. 27, 2022 (Year: 2015).*
Murphy et al (Computational and Structural Biotechnology Journal 14:20-27, 2016) (Year: 2016).*
Pham et al (Current Opinion in Chemical Biology 2013, 17:90-101) (Year: 2013).*
Zhang et al (Nature Chemical Biology (2011), 7(10), 671-677) (Year: 2011).*
Wan et al (Biochimica et Biophysica Acta 1844 (2014) 1059-1070) (Year: 2014).*
Chin et al., Addition of p-azido-L-phenylalanine to the genetic code of *Escherichia coli*, J. Am. Chem. Soc., 124(31):9026-7 (2002).
Chin et al., In vivo photocrosslinking with unnatural amino Acid mutagenesis, Chembiochem., 3(11):1135-7 (Nov. 2002).
Dooley et al., Duchenne muscular dystrophy: a 30-year population-based incidence study, Clin. Pediatr. (Phila.), 49(2):177-9 (Feb. 2010).
Guo et al., tRNA-directed Transcription Antitermination, Prog. Biochem. Biophys., 24(5):392-6 (Dec. 1997).
Henkin, tRNA-directed transcription antitermination, Molecular Microbiol., 13(3):381-7 (1994).
International Application No. PCT/CN2017/07557, Written Opinion of the International Searching Authority (Translation), dated Jun. 14, 2017.
International Application No. PCT/CN2017/075577, International Search Report (translation), dated Jun. 14, 2017.
Keeling et al., Suppression of premature termination codons as a therapeutic approach, Grit. Rev. Biochem. Mol. Biol., 47(5):444-63 (Sep. 2012).
Roy et al., Nonsense suppression by near-cognate tRNAs employs alternative base pairing at codon positions 1 and 3, Proc. Natl. Acad. Sci. USA, 112(10):3038-43 (Mar. 2015).
Wang et al., Expanding the genetic code of *Escherichia coli*, Science, 292(5516):498-500 (Apr. 2001).
Wang et al., Expanding the genetic code, Angew. Chem. Int. Ed. Engl., 44(1):34-66 (Dec. 2004).

(Continued)

*Primary Examiner* — Richard A Schnizer
(74) *Attorney, Agent, or Firm* — Marshall, Gerstein & Borun LLP

(57) ABSTRACT

Provided is a method for high-efficiently reading through a nonsense mutation site in a pathogenic gene in a monogenic hereditary disease and restoring the normal structure and function of a mutant protein, by using a genetic code expanded non-natural amino acid system. By modifying a tRNA of *Methanosarcina barkeri* (tRNAPyl), an all-new UAA and UGA encoded non-natural amino acid system that has high read-through efficiency is obtained, and the range of using the orthogonal pair of tRNAPyl and pyrrolysyl-tRNA synthetase (PylRS) is expanded. A plasmid mimicking the endogenous premature termination codon is constructed, so as to evaluate the efficiency of reading through the endogenous premature termination codon. Also provided is a system mainly comprising pathogenic genes of monogenic hereditary diseases and tumor inhibitory genes in tumor cells.

2 Claims, 7 Drawing Sheets

Specification includes a Sequence Listing.

(56) References Cited

OTHER PUBLICATIONS

Xio et al., "Genetic Incorporation of Multiple Unnatural Amino Acids into Proteins in Mammalian Cells," Angew. Chem. Int. Ed., 52:14080-14083 (2013).

* cited by examiner

The protocol for screening the stable cell line

Structure of Dystrophin protein

SEQUENCE LISTING

<160> NUMBER OF SEQ ID NOS: 44

<210> SEQ ID NO 1
<211> LENGTH: 77
<212> TYPE: RNA
<213> ORGANISM: Artificial Sequence
<220> FEATURE:
<223> OTHER INFORMATION: Synthetic Polynucleotide

<400> SEQUENCE: 1
ggaaaccuga ucauguagau cgaauggacu uuaaauccgu ucagccgggu uagauucccg    60
ggguuuccgc cauuuuu                                                  77

<210> SEQ ID NO 2
<211> LENGTH: 77
<212> TYPE: RNA
<213> ORGANISM: Artificial Sequence
<220> FEATURE:
<223> OTHER INFORMATION: Synthetic Polynucleotide

<400> SEQUENCE: 2
ggaaaccuga ucauguagau cgaauggacu ucaaauccgu ucagccgggu uagauucccg    60
ggguuuccgc cauuuuu                                                  77

<210> SEQ ID NO 3
<211> LENGTH: 1831
<212> TYPE: DNA
<213> ORGANISM: Artificial Sequence
<220> FEATURE:
<223> OTHER INFORMATION: Synthetic Polynucleotide

<400> SEQUENCE: 3
atggaacaaa aactcatctc agaagaggat ctgtcgtcca tcttgccttt caccccgcca    60
gtagtgaagc gcctgctagg atggaagaag tctgcaagtg gcaccacagg agcaggtggc   120
gatgagcaga acggacagga agagaagtgg tgcgaaaaag cggtaaagag cttggtgaaa   180
aaactgaaga aaacgggaca attagacgag cttgagaagg cgatcacgac gcagaactgc   240
aacacgaaat gcgtaacgat accaaggtga gtactccctc tcaaaagcgg gcatgacttc   300
tgccctcgag ttattaaccc tcactaaagg cagtagtcaa gggtttcctt gaagctttcg   360
tgctgaccct gtcccttttt tttccacagc acttgctctg aaatttgggg actgagtaca   420
gcaaatacca tagatcagtg ggataccaca ggcctttaca gcttctctga acaaaccagg   480
tgagtactcc ctctcaaaag cgggcatgac ttctgccctc gagttattaa ccctcactaa   540
aggcagtagt caagggtttc cttgaagctt tcgtgctgac cctgtccctt tttttccac    600 aggtctcttg atggtcgact ccaggtgtct caccgtaaag gattgccgca tgttatctac   660
tgcagactgt ggcgctggcc agacctgcac agtcatcatg aactgaaagc aatcgaaaat   720
tgtgaatatg cttttaacct taaaaaagat gaagtttgtg tcaatccata ccattatcag   780
agggtggaga caccaggtga gtactccctc tcaaaagcgg gcatgacttc tgccctcgag   840
ttattaaccc tcactaaaag gcagtagtca agggtttccc ttgaagcttt cgtgctgacc   900
ctgtcccttt ttttccacag ttttaccacc tgtattagtt ccacggcaca cggaaatctt   960
gacagagctg ccacctcttg atgactacac gcattccatt ccagaaaaca ctaattttcc  1020
tgcagggatt gaacctcaga gcaattatat tccagaaaca ccacctcctg gatatattag  1080
tgaagatgga gaaactagcg atcagcaact taaccaaagc atggacacag gtcaccagc   1140 tgagctgtct ccgagtacac tttctccagt caaccacaat ctcgatttgc aacctgtcac  1200

```
ctattcggaa cctgcttttt ggtgctctat agcatactac gaactgaatc agcgagtagg      1260
agaaactttc catgcatcgc aaccatcgct taccgtggac ggctttacgg acccctcaaa      1320
ctctgaaagg ttctgcttag gtttactctc aaatgtgaac cgaaatgcca cggtggaaat      1380
gaccaggcgt cacataggaa ggggtgtccg gctatattac atcggtggag aggtgtttgc      1440
agagtgccta agtgatagtg ctattttgt tcagagtcca aactgtaacc agcgatatgg       1500
atggcatcca gcaactgtat gtaagattcc tccaggatgc aatctgaaga ttttcaataa      1560
tcaagagttt gcggctctcc tcgctcagtc tgtgaatcaa ggctttgaag cagtttatca      1620
gttaactcga atgtgcacca taaggatgag ctttgtaaaa ggctggggtg ctgaatacag      1680
gcgacagacc gttacaagca ctccatgctg gattgagctt cacctgaatg gacctttgca      1740
gtggttggac aaagtgttga cacagatggg atccccttca gtccgctgct caagcatgtc      1800
ctacccatac gacgtcccag actacgctta a                                    1831
```

<210> SEQ ID NO 4
<211> LENGTH: 1831
<212> TYPE: DNA
<213> ORGANISM: Artificial Sequence
<220> FEATURE:
<223> OTHER INFORMATION: Synthetic Polynucleotide

<400> SEQUENCE: 4

```
atggaacaaa aactcatctc agaagaggat ctgtcgtcca tcttgccttt caccccgcca        60
gtagtgaagc gcctgctagg atggaagaag tctgcaagtg gcaccacagg agcaggtggc       120
gatgagcaga acggacagga agagaagtag tgcgaaaaag cggtaaagag cttggtgaaa       180
aaactgaaga aaacgggaca attagacgag cttgagaagg cgatcacgac gcagaactgc       240
aacacgaaat gcgtaacgat accaaggtga gtactccctc tcaaaagcgg gcatgacttc       300
tgccctcgag ttattaaccc tcactaaagg cagtagtcaa gggtttcctt gaagcttcg        360 tgctgaccct gtcccttttt tttccacagc acttgctctg aaatttgggg actgagtaca       420
gcaaatacca tagatcagtg ggataccaca ggcctttaca gcttctctga acaaaccagg       480
tgagtactcc ctctcaaaag cgggcatgac ttctgccctc gagttattaa ccctcactaa       540
aggcagtagt caagggtttc cttgaagctt tcgtgctgac cctgtccctt ttttttccac       600
aggtctcttg atggtcgact ccaggtgtct caccgtaaag gattgccgca tgttatctac       660
tgcagactgt ggcgctggcc agacctgcac agtcatcatg aactgaaagc aatcgaaaat      720
tgtgaatatg cttttaacct taaaaaagat gaagtttgtg tcaatccata ccattatcag      780
agggtggaga caccaggtga gtactccctc tcaaaagcgg gcatgacttc tgccctcgag       840
ttattaaccc tcactaaaag gcagtagtca agggtttccc ttgaagcttt cgtgctgacc       900
ctgtcccttt ttttccacag ttttaccacc tgtattagtt ccacggcaca cggaaatctt       960
gacagagctg ccacctcttg atgactacac gcattccatt ccagaaaaca ctaatttcc      1020 tgcagggatt gaacctcaga gcaattatat tccagaaaca ccacctcctg atatattag      1080 tgaagatgga gaactagcg atcagcaact taaccaaagc atggacacag gtcaccagc       1140 tgagctgtct ccgagtacac tttctccagt caaccacaat ctcgatttgc aacctgtcac     1200
ctattcggaa cctgcttttt ggtgctctat agcatactac gaactgaatc agcgagtagg     1260
agaaactttc catgcatcgc aaccatcgct taccgtggac ggctttacgg acccctcaaa     1320
ctctgaaagg ttctgcttag gtttactctc aaatgtgaac cgaaatgcca cggtggaaat    1380
```

```
gaccaggcgt cacataggaa ggggtgtccg gctatattac atcggtggag aggtgtttgc   1440
agagtgccta agtgatagtg ctattttgt tcagagtcca aactgtaacc agcgatatgg    1500
atggcatcca gcaactgtat gtaagattcc tccaggatgc aatctgaaga ttttcaataa   1560
tcaagagttt gcggctctcc tcgctcagtc tgtgaatcaa ggctttgaag cagtttatca   1620
gttaactcga atgtgcacca taaggatgag ctttgtaaaa ggctggggtg ctgaatacag   1680
gcgacagacc gttacaagca ctccatgctg gattgagctt cacctgaatg gacctttgca   1740
gtggttggac aaagtgttga cacagatggg atccccttca gtccgctgct caagcatgtc   1800
ctacccatac gacgtcccag actacgctta a                                  1831
```

```
<210> SEQ ID NO 5
<211> LENGTH: 1831
<212> TYPE: DNA
<213> ORGANISM: Artificial Sequence
<220> FEATURE:
<223> OTHER INFORMATION: Synthetic Polynucleotide

<400> SEQUENCE: 5
atggaacaaa aactcatctc agaagaggat ctgtcgtcca tcttgccttt cacccccgcca    60 gtagtgaagc gcctgctagg atggaagaag tctgcaagtg gcaccacagg agcaggtggc   120
gatgagcaga acggacagga agagaagtgg tgcgaaaaag cggtaaagag cttggtgaaa   180
aaactgaaga aaacgggaca attagacgag cttgagaagg cgatcacgac gcagaactgc   240
aacacgaaat gcgtaacgat accaaggtga gtactccctc tcaaaagcgg gcatgacttc   300
tgccctcgag ttattaaccc tcactaaagg cagtagtcaa gggtttcctt gaagctttcg   360
tgctgaccct gtccctttt tttccacagc acttgctctg aaatttgggg actgagtaca   420
gcaaatacca tagatcagtg ggataccaca ggcctttaca gcttctctga acaaaccagg   480
tgagtactcc ctctcaaaag cgggcatgac ttctgccctc gagttattaa ccctcactaa   540
aggcagtagt caagggtttc cttgaagctt tcgtgctgac cctgtccctt ttttttccac   600
aggtctcttg atggtcgact ccaggtgtct caccgtaaag gattgccgca tgttatctac   660
tgcagactgt ggcgctagcc agacctgcac agtcatcatg aactgaaagc aatcgaaaat   720
tgtgaatatg cttttaacct taaaaaagat gaagtttgtg tcaatccata ccattatcag   780
agggtggaga caccaggtga gtactccctc tcaaaagcgg gcatgacttc tgccctcgag   840
ttattaaccc tcactaaaag gcagtagtca agggtttccc ttgaagcttt cgtgctgacc   900 ctgtccctt ttttccacag ttttaccacc tgtattagtt ccacggcaca cggaaatctt   960
gacagagctg ccacctcttg atgactacac gcattccatt ccagaaaaca ctaattttcc   1020
tgcagggatt gaacctcaga gcaattatat tccagaaaca ccacctcctg gatatattag   1080
tgaagatgga gaaactagcg atcagcaact taaccaaagc atggacacag ggtcaccagc   1140
tgagctgtct ccgagtacac tttctccagt caaccacaat ctcgatttgc aacctgtcac   1200
ctattcggaa cctgcttttt ggtgctctat agcatactac gaactgaatc agcgagtagg   1260
agaaactttc catgcatcgc aaccatcgct taccgtggac ggctttacgg accccctcaaa  1320 ctctgaaagg ttctgcttag gtttactctc aaatgtgaac cgaaatgcca cggtggaaat   1380
gaccaggcgt cacataggaa ggggtgtccg gctatattac atcggtggag aggtgtttgc   1440
agagtgccta agtgatagtg ctattttgt tcagagtcca aactgtaacc agcgatatgg    1500
atggcatcca gcaactgtat gtaagattcc tccaggatgc aatctgaaga ttttcaataa   1560
tcaagagttt gcggctctcc tcgctcagtc tgtgaatcaa ggctttgaag cagtttatca   1620
```

| | |
|---|---:|
| gttaactcga atgtgcacca taaggatgag ctttgtaaaa ggctggggtg ctgaatacag | 1680 |
| gcgacagacc gttacaagca ctccatgctg gattgagctt cacctgaatg gacctttgca | 1740 |
| gtggttggac aaagtgttga cacagatggg atccccttca gtccgctgct caagcatgtc | 1800 |
| ctacccatac gacgtcccag actacgctta a | 1831 |

<210> SEQ ID NO 6
<211> LENGTH: 1831
<212> TYPE: DNA
<213> ORGANISM: Artificial Sequence
<220> FEATURE:
<223> OTHER INFORMATION: Synthetic Polynucleotide

<400> SEQUENCE: 6

| | |
|---|---:|
| atggaacaaa aactcatctc agaagaggat ctgtcgtcca tcttgccttt caccccgcca | 60 |
| gtagtgaagc gcctgctagg atggaagaag tctgcaagtg gcaccacagg agcaggtggc | 120 |
| gatgagcaga acgacagga agagaagtgg tgcgaaaaag cggtaaagag cttggtgaaa | 180 |
| aaactgaaga aaacgggaca attagacgag cttgagaagg cgatcacgac gcagaactgc | 240 |
| aacacgaaat gcgtaacgat accaaggtga gtactccctc tcaaaagcgg gcatgacttc | 300 |
| tgccctcgag ttattaaccc tcactaaagg cagtagtcaa gggtttcctt gaagctttcg | 360 |
| tgctgaccct gtccctttt tttccacagc acttgctctg aaatttgggg actgagtaca | 420 |
| gcaaatacca tagatcagtg ggataccaca ggcctttaca gcttctctga acaaaccagg | 480 |
| tgagtactcc ctctcaaaag cgggcatgac ttctgccctc gagttattaa ccctcactaa | 540 |
| aggcagtagt caagggtttc cttgaagctt tcgtgctgac cctgtccctt tttttccac | 600 |
| aggtctcttg atggtcgact ccaggtgtct caccgtaaag gatagccgca tgttatctac | 660 |
| tgcagactgt ggcgctggcc agacctgcac agtcatcatg aactgaaagc aatcgaaaat | 720 |
| tgtgaatatg cttttaacct taaaaagat gaagtttgtg tcaatccata ccattatcag | 780 |
| agggtggaga caccaggtga gtactccctc tcaaaagcgg gcatgacttc tgccctcgag | 840 |
| ttattaaccc tcactaaaag gcagtagtca agggtttccc ttgaagcttt cgtgctgacc | 900 |
| ctgtcccttt tttccacag ttttaccacc tgtattagtt ccacggcaca cggaaatctt | 960 |
| gacagagctg ccacctcttg atgactacag gcattccatt ccagaaaaca ctaattttcc | 1020 |
| tgcagggatt gaacctcaga gcaattatat tccagaaaca ccacctcctg gatatattag | 1080 |
| tgaagatgga gaaactagcg atcagcaact taaccaaagc atggacacag ggtcaccagc | 1140 |
| tgagctgtct ccgagtacac tttctccagt caaccacaat ctcgatttgc aacctgtcac | 1200 |
| ctattcggaa cctgcttttt ggtgctctat agcatactac gaactgaatc agcgagtagg | 1260 |
| agaaactttc catgcatcgc aaccatcgct taccgtggac ggctttacgg acccctcaaa | 1320 |
| ctctgaaagg ttctgcttag gtttactctc aaatgtgaac cgaaatgcca cggtggaaat | 1380 |
| gaccaggcgt cacataggaa ggggtgtccg gctatattac atcggtggag aggtgtttgc | 1440 |
| agagtgccta agtgatagtg ctatttttgt tcagagtcca aactgtaacc agcgatatgg | 1500 |
| atggcatcca gcaactgtat gtaagattcc tccaggatgc aatctgaaga ttttcaataa | 1560 |
| tcaagagttt gcggctctcc tcgctcagtc tgtgaatcaa ggcttgaag cagttttatca | 1620 |
| gttaactcga atgtgcacca taaggatgag ctttgtaaaa ggctggggtg ctgaatacag | 1680 |
| gcgacagacc gttacaagca ctccatgctg gattgagctt cacctgaatg gacctttgca | 1740 |
| gtggttggac aaagtgttga cacagatggg atccccttca gtccgctgct caagcatgtc | 1800 |

```
ctacccatac gacgtcccag actacgctta a                                      1831

<210> SEQ ID NO 7
<211> LENGTH: 717
<212> TYPE: DNA
<213> ORGANISM: Aequorea victoria

<400> SEQUENCE: 7
gtgagcaagg gcgaggagct gttcaccggg gtggtgccca tcctggtcga gctggacggc       60
gacgtaaacg gccacaagtt cagcgtgtcc ggcgagggcg agggcgatgc cacctacggc      120
aagctgaccc tgaagttcat ctgcaccacc ggcaagctgc ccgtgccctg ccccaccctc      180
gtgaccaccc tgacctacgg cgtgcagtgc ttcagccgct accccgacca catgaagcag      240
cacgacttct tcaagtccgc catgcccgaa ggctacgtcc aggagcgcac catcttcttc      300
aaggacgacg gcaactacaa gacccgcgcc gaggtgaagt tcgagggcga caccctggtg      360
aaccgcatcg agctgaaggg catcgacttc aaggaggacg gcaacatcct ggggcacaag      420
ctggagtaca actacaacag ccacaacgtc tatatcatgg ccgacaagca gaagaacggc      480
atcaaggtga acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccgccct gagcaaagac cccaacgaga gcgcgatca catggtcctg       660 ctggagttcg tgaccgccgc cgggatcact ctcggcatgg acgagctgta caagtaa        717

<210> SEQ ID NO 8
<211> LENGTH: 8483
<212> TYPE: DNA
<213> ORGANISM: Artificial Sequence
<220> FEATURE:
<223> OTHER INFORMATION: Synthetic Polynucleotide

<400> SEQUENCE: 8
gacgaaaggg cctcgtgata cgcctatttt tataggttaa tgtcatgata ataatggttt       60
cttagacgtc aggtggcact tttcggggaa atgtgcgcgg aacccctatt tgtttatttt      120
tctaaataca ttcaaatatg tatccgctca tgagacaata accctgataa atgcttcaat      180
aatattgaaa aaggaagagt atgagtattc aacatttccg tgtcgccctt attcccttt       240 ttgcggcatt ttgccttcct gttttttgctc acccagaaac gctggtgaaa gtaaaagatg      300
ctgaagatca gttgggtgca cgagtgggtt acatcgaact ggatctcaac agcggtaaga      360
tccttgagag ttttcgcccc gaagaacgtt ttccaatgat gagcactttt aaagttctgc      420
tatgtggcgc ggtattatcc cgtattgacg ccgggcaaga gcaactcggt cgccgcatac      480
actattctca gaatgacttg gttgagtact caccagtcac agaaaagcat cttacggatg      540
gcatgacagt aagagaatta tgcagtgctg ccataaccat gagtgataac actgcggcca      600
acttacttct gacaacgatc ggaggaccga aggagctaac cgcttttttg cacaacatgg      660
gggatcatgt aactcgcctt gatcgttggg aaccggagct gaatgaagcc ataccaaacg      720
acgagcgtga ccaccgatg cctgtagcaa tggcaacaac gttgcgcaaa ctattaactg      780
gcgaactact tactctagct tcccggcaac aattaataga ctggatggag gcggataaag      840
ttgcaggacc acttctgcgc tcggcccttc cggctggctg gtttattgct gataaatctg      900
gagccggtga gcgtgggtct cgcggtatca ttgcagcact ggggccagat ggtaagccct      960
cccgtatcgt agttatctac acgacgggga gtcaggcaac tatggatgaa cgaaatagac     1020
agatcgctga gataggtgcc tcactgatta agcattggta actgtcagac caagtttact     1080
```

```
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttgtga tgctcgtcag   1800 gggggcggag cctatggaaa aacgccagca acgcggcctt tttacggttc ctggcctttt   1860
gctggccttt tgctcacatg ttctttcctg cgttatcccc tgattctgtg ataaccgta   1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gcatgcctgc aggtcgacga acgctgacgt catcaacccg   2280
ctccaaggaa tcgcgggccc agtgtcacta ggcgggaaca cccagcgcgc gtgcgccctg   2340
gcaggaagat ggctgtgagg gacaggggag tggcgccctg caatatttgc atgtcgctat   2400
gtgttctggg aaatcaccat aaacgtgaaa tgtctttgga tttgggaatc ttataagttc   2460
tgtatgagac cacagatccc cggaaacctg atcatgtaga tcgaatggac tctaaatccg   2520
ttcagccggg ttagattccc ggggtttccg ccattttttct cgacgacgcc gccatctcta   2580
ggcccgcgcc ggccccctcg cacagacttg tgggagaagc tcggctactc ccctgccccg   2640
gttaatttgc atataatatt tcctagtaac tatagaggct taatgtgcga taaaagacag   2700
ataatctgtt cttttttaata ctagctacat tttacatgat aggcttggat ttctataaga   2760
gatacaaata ctaaattatt attttaaaaa acagcacaaa aggaaactca ccctaactgt   2820
aaagtaattg tgtgttttga gactataaat atcccttgga gaaaagcctt gtttggaaac   2880
ctgatcatgt agatcgaatg gactctaaat ccgttcagcc gggttagatt cccggggttt   2940
ccgccatttt tctcgacaag gtcgggcagg aagagggcct atttcccatg attccttcat   3000
atttgcatat acgatacaag gctgttagag agataattag aattaatttg actgtaaaca   3060
caaagatatt agtacaaaat acgtgacgta gaaagtaata atttcttggg tagtttgcag   3120
ttttaaaatt atgttttaaa atggactatc atatgcttac cgtaacttga agtatttcg   3180 atttcttggc tttatatatc ttgtggaaag gacgaaacac cggaaacctg atcatgtaga   3240
tcgaatggac tctaaatccg ttcagccggg ttagattccc ggggtttccg ccatttttct   3300
cgacgaacgc tgacgtcatc aacccgctcc aaggaatcgc gggcccagtg tcactaggcg   3360 ggaacacccca gcgcgcgtgc gccctggcag gaagatggct gtgagggaca ggggagtggc   3420
```

```
gccctgcaat atttgcatgt cgctatgtgt tctgggaaat caccataaac gtgaaatgtc    3480
tttggatttg ggaatcttat aagttctgta tgagaccaca gatccccgga aacctgatca    3540
tgtagatcga atggactcta aatccgttca gccgggttag attcccgggg tttccgccat    3600
ttttctcgac gacgccgcca tctctaggcc cgcgccggcc ccctcgcaca gacttgtggg    3660
agaagctcgg ctactcccct gccccggtta atttgcatat aatatttcct agtaactata    3720
gaggcttaat gtgcgataaa agacagataa tctgttcttt ttaatactag ctacatttta    3780
catgataggc ttggatttct ataagagata caaatactaa attattattt taaaaaacag    3840
cacaaaagga aactcaccct aactgtaaag taattgtgtg ttttgagact ataaatatcc    3900
cttggagaaa agccttgttt ggaaacctga tcatgtagat cgaatggact ctaaatccgt    3960
tcagccgggt tagattcccg ggttttccgc cattttctc gacaaggtcg ggcaggaaga    4020
gggcctattt cccatgattc cttcatattt gcatatacga tacaaggctg ttagagagat    4080
aattagaatt aatttgactg taaacacaaa gatattagta caaatacgt gacgtagaaa    4140 gtaataattt cttgggtagt ttgcagtttt aaaattatgt tttaaaatgg actatcatat    4200
gcttaccgta acttgaaagt atttcgattt cttggctta tatatcttgt ggaaaggacg    4260
aaacaccgga aacctgatca tgtagatcga atggactcta aatccgttca gccgggttag    4320
attcccgggg tttccgccat ttttctcgac tctagaggat ccctgcagta tttagcatgc    4380
cccacccatc tgcaaggcat tctggatagt gtcaaaacag ccggaaatca agtccgttta    4440
tctcaaactt tagcatttg ggaataaatg atatttgcta tgctggttaa attagatttt    4500
agttaaattt cctgctgaag ctctagtacg ataagtaact tgacctaagt gtaaagttga    4560
gatttccttc aggtttatat agcttgtgcg ccgcctgggt acctcggaaa cctgatcatg    4620
tagatcgaat ggactctaaa tccgttcagc cgggttagat tcccggggtt tccgccattt    4680
ttggatctaa ggtcgggcag gaagagggcc tatttcccat gattccttca tatttgcata    4740
tacgatacaa gctgttaga gagataatta gaattaatt gactgtaaac acaaagatat    4800
tagtacaaaa tacgtgacgt agaaagtaat aatttcttgg gtagtttgca gttttaaaat    4860
tatgttttaa aatggactat catatgctta ccgtaacttg aaagtatttc gatttcttgg    4920
ctttatatat cttgtggaaa ggacgaaaca ccggaaacct gatcatgtag atcgaatgga    4980
ctctaaatcc gttcagccgg ttagattcc ggggtttcc gccattttg gatctgaacg    5040 ctgacgtcat caacccgctc caaggaatcg cgggcccagt gtcactaggc gggaacaccc    5100
agcgcgcgtg cgccctggca ggaagatggc tgtgagggac aggggagtgg cgccctgcaa    5160
tatttgcatg tcgctatgtg ttctgggaaa tcaccataaa cgtgaaatgt ctttggattt    5220
gggaatctta aagttctgt atgagaccac agatccccgg aaacctgatc atgtagatcg    5280
aatggactct aaatccgttc agccgggtta gattcccggg gtttccgcca ttttggatc    5340 tctgcagtat ttagcatgcc ccacccatct gcaaggcatt ctggatagtg tcaaaacagc    5400
cggaaatcaa gtccgtttat ctcaaacttt agcattttgg gaataaatga tatttgctat    5460
gctggttaaa ttagatttta gttaaatttc ctgctgaagc tctagtacga taagtaactt    5520
gacctaagtg taaagttgag atttccttca ggtttatata gcttgtgcgc cgcctgggta    5580
cctcggaaac ctgatcatgt agatcgaatg gactctaaat ccgttcagcc gggttagatt    5640 cccgggtt ccgccattt tggatctaag gtcgggcagg aagagggcct atttcccatg    5700
attccttcat atttgcatat acgatacaag gctgttagag agataattag aattaatttg    5760
actgtaaaca caaagatatt agtacaaaat acgtgacgta gaaagtaata atttcttggg    5820
```

-continued

```
tagtttgcag ttttaaaatt atgttttaaa atggactatc atatgcttac cgtaacttga    5880
aagtatttcg atttcttggc tttatatatc ttgtggaaag gacgaaacac cggaaacctg    5940
atcatgtaga tcgaatggac tctaaatccg ttcagccggg ttagattccc ggggtttccg    6000 ccattttttgg atctgaacgc tgacgtcatc aacccgctcc aaggaatcgc gggcccagtg   6060
tcactaggcg ggaacaccca gcgcgcgtgc gccctggcag aagatggct gtgagggaca     6120 ggggagtggc gccctgcaat atttgcatgt cgctatgtgt tctgggaaat caccataaac    6180
gtgaaatgtc tttggatttg ggaatcttat aagttctgta tgagaccaca gatccccgga    6240
aacctgatca tgtagatcga atggactcta aatccgttca gccgggttag attcccgggg    6300
tttccgccat ttttggatct ccgggtaccc tgtgccttct agttgccagc catctgttgt    6360
ttgcccctcc cccgtgcctt ccttgaccct ggaaggtgcc actcccactg tcctttccta    6420
ataaaatgag gaaattgcat cgcattgtct gagtaggtgt cattctattc tggggggtgg    6480
ggtggggcag gacagcaagg gggaggattg gaagacaat agcaggcatg ctggggatgc     6540
ggtgggctct atggcttctg aggcggaaag aaccagctgg ggctctaggg ggtatcccca    6600
cgcgccctgt agcggcgcat taagcgcggc gggtgtggtg gttacgcgca gcgtgaccgc    6660
tacacttgcc agcgccctag cgcccgctcc tttcgctttc ttcccttcct ttctcgccac    6720
gttcgccggc tttccccgtc aagctctaaa tcggggcatc cctttagggt tccgatttag    6780
tgctttacgg cacctcgacc ccaaaaaact tgattagggt gatggttcac gtagtgggcc    6840
atcgccctga tagacggttt ttcgcccttt gacgttggag tccacgttct ttaatagtgg    6900
actcttgttc caaactggaa caacactcaa ccctatctcg gtctattctt ttgatttata    6960
agggattttg gggatttcgg cctattggtt aaaaaatgag ctgatttaac aaaaatttaa    7020
cgcgaattaa ttctgtggaa tgtgtgtcag ttagggtgtg gaaagtcccc aggctcccca    7080
ggcaggcaga agtatgcaaa gcatgcatct caattagtca gcaaccaggt gtggaaagtc    7140
cccaggctcc ccagcaggca gaagtatgca aagcatgcat ctcaattagt cagcaaccat    7200
agtcccgccc ctaactccgc ccatcccgcc cctaactccg cccagttccg cccattctcc    7260
gccccatggc tgactaattt tttttattta tgcagaggcc gaggccgcct ctgcctctga    7320
gctattccag aagtagtgag gaggcttttt tggaggccta ggcttttgca aaaagctccc    7380
gggagcttgt atatccattt tcggaattca tggccaagtt gaccagtgcc gttccggtgc    7440
tcaccgcgcg cgacgtcgcc ggagcggtcg agttctggac cgaccggctc gggttctccc    7500
gggacttcgt ggaggacgac ttcgccggtg tggtccggga cgacgtgacc ctgttcatca    7560
gcgcggtcca ggaccaggtg gtgccggaca cacccctggc ctgggtgtgg gtgcgcggcc    7620
tggacgagct gtacgccgag tggtcggagg tcgtgtccac gaacttccgg gacgcctccg    7680
ggccggccat gaccgagatc ggcgagcagc cgtggggggcg ggagttcgcc ctgcgcgacc    7740
cggccggcaa ctgcgtgcac ttcgtggccg aggagcagga ctgagcggga ctctggggtt    7800
cgaaatgacc gaccaagcga cgcccaacct gccatcacga gatttcgatt ccaccgccgc    7860
cttctatgaa aggttgggct tcggaatcgt tttccgggac gccggctgga tgatcctcca    7920
gcgcggggat ctcatgctgg agttcttcgc ccaccccaac ttgtttattg cagcttataa    7980
tggttacaaa taaagcaata gcatcacaaa tttcacaaat aaagcatttt tttcactgca    8040
ttctagttgt ggtttgtcca aactcatcaa tgtatcttat catgtctgac tggccgtcgt    8100
tttacaacgt cgtgactggg aaaaccctgg cgttacccca cttaatcgcc ttgcagcaca    8160
```

-continued

| | |
|---|---|
| tcccccttc gccagctggc gtaatagcga agaggcccgc accgatcgcc cttcccaaca | 8220 |
| gttgcgcagc ctgaatggcg aatgcgcct gatgcggtat tttctcctta cgcatctgtg | 8280 |
| cggtatttca caccgcatat ggtgcactct cagtacaatc tgctctgatg ccgcatagtt | 8340 |
| aagccagccc cgacacccgc caacacccgc tgacgcgccc tgacgggctt gtctgctccc | 8400 |
| ggcatccgct tacagacaag ctgtgaccgt ctccgggagc tgcatgtgtc agaggttttc | 8460 |
| accgtcatca ccgaaacgcg cga | 8483 |

<210> SEQ ID NO 9
<211> LENGTH: 2001
<212> TYPE: DNA
<213> ORGANISM: Homo sapiens

<400> SEQUENCE: 9

| | |
|---|---|
| atgagggaac agctcaaagg ccacgagact caaacaactt gctgggacca tcccaaaatg | 60 |
| acagagctct accagtcttt agctgacctg aataatgtca gattctcagc ttataggact | 120 |
| gccatgaaac tccgaagact gcagaaggcc ctttgcttgg atctcttgag cctgtcagct | 180 |
| gcatgtgatg ccttggacca gcacaacctc aagcaaaatg accagcccat ggatatcctg | 240 |
| cagattatta attgtttgac cactatttat gaccgcctgg agcaagagca acaatttg | 300 |
| gtcaacgtcc ctctctgcgt ggatatgtgt ctgaactggc tgctgaatgt ttatgatacg | 360 |
| ggacgaacag ggaggatccg tgtcctgtct tttaaaactg gcatcatttc cctgtgtaaa | 420 |
| gcacatttgg aagacaagta cagatacctt ttcaagcaag tggcaagttc aacaggattt | 480 |
| tgtgaccagc gcaggctggg cctccttctg catgattcta tccaaattcc aagacagttg | 540 |
| ggtgaagttg catcctttgg gggcagtaac attgagccaa gtgtccggag ctgcttccaa | 600 |
| tttgctaata taagccaga gatcgaagcg ccctcttcc tagactggat gagactggaa | 660 |
| ccccagtcca tggtgtggct gcccgtcctg cacagagtgg ctgctgcaga aactgccaag | 720 |
| catcaggcca aatgtaacat ctgcaaagag tgtccaatca ttggattcag gtacaggagt | 780 |
| ctaaagcact taattatga catctgccaa agctgctttt tttctggtcg agttgcaaaa | 840 |
| ggccataaaa tgcactatcc catggtggaa tattgcactc cgactacatc aggagaagat | 900 |
| gttcgagact ttgccaaggt actaaaaaac aaatttcgaa ccaaaaggta ttttgcgaag | 960 |
| catccccgaa tgggctacct gccagtgcag actgtcttag aggggggacaa catggaaact | 1020 |
| cccgttactc tgatcaactt ctggccagta gattctgcgc ctgcctcgtc ccctcagctt | 1080 |
| tcacacgatg atactcattc acgcattgaa cattatgcta gcaggctagc agaaatggaa | 1140 |
| aacagcaatg gatcttatct aaatgatagc atctctccta tgagagcat agatgatgaa | 1200 |
| catttgttaa tccagcatta ctgccaaagt ttgaaccagg actcccccct gagccagcct | 1260 |
| cgtagtcctg cccagatctt gatttcctta gagagtgagg aaagagggga gctagagaga | 1320 |
| atcctagcag atcttgagga agaaaacagg aatctgcaag cagaatatga ccgtctaaag | 1380 |
| cagcagcacg aacataaagg cctgtcccca ctgccgtccc ctcctgaaat gatgcccacc | 1440 |
| tctcccccaga gtccccggga tgctgagctc attgctgagg ccaagctact gcgtcaacac | 1500 |
| aaaggccgcc tggaagccag gatgcaaatc tggaagacc acaataaaca gctggagtca | 1560 |
| cagttacaca ggctaaggca gctgctggag caaccccagg cagaggccaa agtgaatggc | 1620 |
| acaacggtgt cctctccttc tacctctcta cagaggtccg acagcagtca gcctatgctg | 1680 |
| ctccgagtgg ttggcagtca aacttcggac tccatgggtg aggaagatct tctcagtcct | 1740 |
| ccccaggaca caagcacagg gttagaggag gtgatggagc aactcaacaa ctccttccct | 1800 |

| agttcaagag gacacaatgt aggaagtctt ttccacatgg cagatgattt gggcagagcg | 1860 |
| atggagtcct tagtatcagt catgacagat gaagaaggac agaaacgcg tacgcggccg | 1920 |
| ctcgagcaga aactcatctc agaagaggat ctggcagcaa atgatatcct ggattacaag | 1980 |
| gatgacgacg ataaggttta a | 2001 |

<210> SEQ ID NO 10
<211> LENGTH: 2001
<212> TYPE: DNA
<213> ORGANISM: Artificial Sequence
<220> FEATURE:
<223> OTHER INFORMATION: Synthetic Polynucleotide

<400> SEQUENCE: 10

| atgagggaac agctcaaagg ccacgagact caaacaactt gctgggacca tcccaaaatg | 60 |
| acagagctct accagtcttt agctgacctg aataatgtca gattctcagc ttataggact | 120 |
| gccatgaaac tccgaagact gtagaaggcc ctttgcttgg atctcttgag cctgtcagct | 180 |
| gcatgtgatg ccttggacca gcacaacctc aagcaaaatg accagcccat ggatatcctg | 240 |
| cagattatta attgtttgac cactatttat gaccgcctgg agcaagagca caacaatttg | 300 |
| gtcaacgtcc ctctctgcgt ggatatgtgt ctgaactggc tgctgaatgt ttatgatacg | 360 |
| ggacgaacag ggaggatccg tgtcctgtct tttaaaactg gcatcatttc cctgtgtaaa | 420 |
| gcacatttgg aagacaagta cagataccct ttcaagcaag tggcaagttc aacaggattt | 480 |
| tgtgaccagc gcaggctggg cctccttctg catgattcta tccaaattcc aagacagttg | 540 |
| ggtgaagttg catcctttgg gggcagtaac attgagccaa gtgtccggag ctgcttccaa | 600 |
| tttgctaata ataagccaga gatcgaagcg gccctcttcc tagactggat gagactggaa | 660 |
| cccccagtcca tggtgtggct gcccgtcctg cacagagtgg ctgctgcaga aactgccaag | 720 |
| catcaggcca aatgtaacat ctgcaaagag tgtccaatca ttggattcag gtacaggagt | 780 |
| ctaaagcact ttaattatga catctgccaa agctgctttt tttctggtcg agttgcaaaa | 840 |
| ggccataaaa tgcactatcc catggtggaa tattgcactc cgactacatc aggagaagat | 900 |
| gttcgagact ttgccaaggt actaaaaaac aaatttcgaa ccaaaaggta ttttgcgaag | 960 |
| catccccgaa tgggctacct gccagtgcag actgtcttag agggggacaa catggaaact | 1020 |
| cccgttactc tgatcaactt ctggccagta gattctgcgc ctgcctcgtc ccctcagctt | 1080 |
| tcacacgatg atactcattc acgcattgaa cattatgcta gcaggctagc agaaatggaa | 1140 |
| aacagcaatg gatcttatct aaatgatagc atctctccta atgagagcat agatgatgaa | 1200 |
| catttgttaa tccagcatta ctgccaaagt ttgaaccagg actccccct gagccagcct | 1260 |
| cgtagtcctg cccagatctt gatttcctta gagagtgagg aaagagggga gctagagaga | 1320 |
| atcctagcag atcttgagga agaaaacagg aatctgcaag cagaatatga ccgtctaaag | 1380 |
| cagcagcacg aacataaagg cctgtcccca ctgccgtccc ctcctgaaat gatgccacc | 1440 |
| tctccccaga gtccccggga tgctgagctc attgctgagg ccaagctact cgtcaacac | 1500 |
| aaaggccgcc tggaagccag gatgcaaatc ctggaagacc acaataaaca gctggagtca | 1560 |
| cagttacaca ggctaaggca gctgctggag caaccccagg cagaggccaa agtgaatggc | 1620 |
| acaacggtgt cctctccttc tacctctcta cagaggtccg acagcagtca gcctatgctg | 1680 |
| ctccgagtgg ttggcagtca aacttcggac tccatgggtg aggaagatct tctcagtcct | 1740 |
| ccccaggaca caagcacagg gttagaggag gtgatggagc aactcaacaa ctccttccct | 1800 |

| | |
|---|---|
| agttcaagag gacacaatgt aggaagtctt ttccacatgg cagatgattt gggcagagcg | 1860 |
| atggagtcct tagtatcagt catgacagat gaagaaggag cagaaacgcg tacgcggccg | 1920 |
| ctcgagcaga aactcatctc agaagaggat ctggcagcaa atgatatcct ggattacaag | 1980 |
| gatgacgacg ataaggttta a | 2001 |

```
<210> SEQ ID NO 11
<211> LENGTH: 2001
<212> TYPE: DNA
<213> ORGANISM: Artificial Sequence
<220> FEATURE:
<223> OTHER INFORMATION: Synthetic Polynucleotide

<400> SEQUENCE: 11
```

| | |
|---|---|
| atgagggaac agctcaaagg ccacgagact caaacaactt gctgggacca tcccaaaatg | 60 |
| acagagctct accagtcttt agctgacctg aataatgtca gattctcagc ttataggact | 120 |
| gccatgaaac tccgaagact gcagaaggcc ctttgcttgg atctcttgag cctgtcagct | 180 |
| gcatgtgatg ccttggacca gcacaacctc aagcaaaatg accagcccat ggatatcctg | 240 |
| cagattatta attgtttgac cactatttat gaccgcctgg agcaagagca caacaatttg | 300 |
| gtcaacgtcc ctctctgcgt ggatatgtgt ctgaactggc tgctgaatgt ttatgatacg | 360 |
| ggacgaacag ggaggatccg tgtcctgtct tttaaaactg gcatcatttc cctgtgtaaa | 420 |
| gcacatttgg aagacaagta cagatacctt ttcaagcaag tggcaagttc aacaggattt | 480 |
| tgtgaccagc gcaggctggg cctccttctg catgattcta tccaaattcc aagacagttg | 540 |
| ggtgaagtta catcctttgg gggcagtaac attgagccaa gtgtccggag ctgcttccaa | 600 |
| tttgctaata ataagccaga gatcgaagcg ccctcttcc tagactggat gagactggaa | 660 |
| ccccagtcca tggtgtggct gcccgtcctg cacagagtgg ctgctgcaga aactgccaag | 720 |
| catcaggcca aatgtaacat ctgcaaatag tgtccaatca ttggattcag gtacaggagt | 780 |
| ctaaagcact taattatga catctgccaa agctgctttt tttctggtcg agttgcaaaa | 840 |
| ggccataaaa tgcactatcc catggtggaa tattgcactc cgactacatc aggagaagat | 900 |
| gttcgagact ttgccaaggt actaaaaaac aaatttcgaa ccaaaaggta ttttgcgaag | 960 |
| catccccgaa tgggctacct gccagtgcag actgtcttag aggggacaa catggaaact | 1020 |
| cccgttactc tgatcaactt ctggccagta gattctgcgc tgcctcgtc ccctcagctt | 1080 |
| tcacacgatg atactcattc acgcattgaa cattatgcta gcaggctagc agaaatggaa | 1140 |
| aacagcaatg gatcttatct aaatgatagc atctctccta atgagagcat agatgatgaa | 1200 |
| catttgttaa tccagcatta ctgccaaagt ttgaaccagg actccccct gagccagcct | 1260 |
| cgtagtcctg cccagatctt gatttcctta gagagtgagg aaagagggga gctagagaga | 1320 |
| atcctagcag atcttgagga agaaaacagg aatctgcaag cagaatatga ccgtctaaag | 1380 |
| cagcagcacg aacataaagg cctgtcccca ctgcctgtcc ctcctgaaat gatgcccacc | 1440 |
| tctcccccaga gtccccggga tgctgagctc attgctgagg ccaagctact gcgtcaacac | 1500 |
| aaaggccgcc tggaagccag gatgcaaatc ctggaagacc acaataaaca gctggagtca | 1560 |
| cagttacaca ggctaaggca gctgctggag caacccagg cagaggccaa agtgaatggc | 1620 |
| acaacggtgt cctctccttc tacctctcta cagaggtccg acagcagtca gcctatgctg | 1680 |
| ctccgagtgg ttggcagtca aacttcggac tccatgggtg aggaagatct tctcagtcct | 1740 |
| ccccaggaca caagcacagg gttagaggag gtgatggagc aactcaacaa ctccttccct | 1800 |
| agttcaagag gacacaatgt aggaagtctt ttccacatgg cagatgattt gggcagagcg | 1860 |

```
atggagtcct tagtatcagt catgacagat gaagaaggag cagaaacgcg tacgcggccg    1920
ctcgagcaga aactcatctc agaagaggat ctggcagcaa atgatatcct ggattacaag    1980
gatgacgacg ataaggttta a                                              2001
```

<210> SEQ ID NO 12
<211> LENGTH: 2001
<212> TYPE: DNA
<213> ORGANISM: Artificial Sequence
<220> FEATURE:
<223> OTHER INFORMATION: Synthetic Polynucleotide

<400> SEQUENCE: 12

```
atgagggaac agctcaaagg ccacgagact caaacaactt gctgggacca tcccaaaatg      60
acagagctct accagtcttt agctgacctg aataatgtca gattctcagc ttataggact     120
gccatgaaac tccgaagact gcagaaggcc ctttgcttgg atctcttgag cctgtcagct     180
gcatgtgatg ccttggacca gcacaacctc aagcaaaatg accagcccat ggatatcctg     240
cagattatta attgtttgac cactatttat gaccgcctgg agcaagagca acaatttg      300 gtcaacgtcc ctctctgcgt ggatatgtgt ctgaactggc tgctgaatgt ttatgatacg     360
ggacgaacag ggaggatccg tgtcctgtct tttaaaactg gcatcatttc cctgtgtaaa     420
gcacatttgg aagacaagta cagataccct tcaagcaag tggcaagttc aacaggatt     480 tgtgaccagc gcaggctggg cctccttctg catgattcta tccaaattcc aagacagttg     540
ggtgaagttg catcctttgg gggcagtaac attgagccaa gtgtccggag ctgcttccaa     600
tttgctaata ataagccaga gatcgaagcg gccctcttcc tagactggat gagactggaa     660
ccccagtcca tggtgtggct gcccgtcctg cacagagtgg ctgctgcaga aactgccaag     720
catcaggcca aatgtaacat ctgcaaagag tgtccaatca ttggattcag gtacaggagt     780
ctaaagcact taattatga catctgccaa agctgctttt tttctggtcg agttgcaaaa     840
ggccataaaa tgcactatcc catggtggaa tattgcactc cgactacatc aggagaagat     900
gttcgagact ttgccaaggt actaaaaaac aaattcgaa ccaaaaggta ttttgcgaag     960
catccccgaa tgggctacct gccagtgcag actgtcttag aggggacaa catggaaact    1020 cccgttactc tgatcaactt ctggccagta gattctgcgc ctgcctcgtc ccctcagctt    1080
tcacacgatg atactcattc acgcattgaa cattatgcta gcaggctagc agaaatggaa    1140
aacagcaatg gatcttatct aaatgatagc atctctccta tgagagcat agatgatgaa    1200 catttgttaa tccagcatta ctgccaaagt ttgaaccagg actccccct gagccagcct    1260 cgtagtcctg cccagatctt gatttcctta gagagtgagg aaagagggga gctagagaga    1320
atcctagcag atcttgagga agaaaacagg aatctgcaag cagaatatga ccgtctaaag    1380
cagcagcacg aacataaagg cctgtcccca ctgccgtccc ctcctgaaat gatgccacc    1440 tctcccagag tccccggga tgctgagctc attgctgagg ccaagctact cgtcaacac    1500 aaaggccgcc tggaagccag gatgcaaatc ctggaagacc acaataaaca gctggagtca    1560
cagttacaca ggctaaggca gctgctggag caaccctagg cagaggccaa agtgaatggc    1620
acaacggtgt cctctccttc tacctctcta cagaggtccg acagcagtca gcctatgctg    1680
ctccgagtgg ttggcagtca aacttcggac tccatgggtg aggaagatct tctcagtcct    1740
ccccaggaca caagcacagg gttagaggag gtgatggagc aactcaacaa ctccttccct    1800
agttcaagag gacacaatgt aggaagtctt ttccacatgg cagatgattt gggcagagcg    1860
```

```
atggagtcct tagtatcagt catgacagat gaagaaggag cagaaacgcg tacgcggccg    1920
ctcgagcaga aactcatctc agaagaggat ctggcagcaa atgatatcct ggattacaag    1980
gatgacgacg ataaggttta a                                              2001
```

<210> SEQ ID NO 13
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UAA-for

<400> SEQUENCE: 13

```
tgtagatcga atggacttta aatccgttca gccgg                               35
```

<210> SEQ ID NO 14
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UAA-rev

<400> SEQUENCE: 14

```
ccggctgaac ggatttaaag tccattcgat ctaca                               35
```

<210> SEQ ID NO 15
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UGA-for

<400> SEQUENCE: 15

```
catgtagatc gaatggactt caaatccgtt cagccgggtt                          40
```

<210> SEQ ID NO 16
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UGA-rev

<400> SEQUENCE: 16

```
aacccggctg aacggatttg aagtccattc gatctacatg                          40
```

<210> SEQ ID NO 17
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UAA-for

<400> SEQUENCE: 17
tgtagatcga atggacttta aatccgttca gccgg                                      35

<210> SEQ ID NO 18
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UAA-rev

<400> SEQUENCE: 18
ccggctgaac ggatttaaag tccattcgat ctaca                                      35

<210> SEQ ID NO 19
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UGA-for

<400> SEQUENCE: 19
catgtagatc gaatggactt caaatccgtt cagccgggtt                                 40

<210> SEQ ID NO 20
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PCMV-UAG-UGA-rev

<400> SEQUENCE: 20
aacccggctg aacggatttg aagtccattc gatctacatg                                 40

<210> SEQ ID NO 21
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 21
ggcgagggcg atgccaccta gggcaagctg accctgaagt tc                              42

<210> SEQ ID NO 22
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 22
gaacttcagg gtcagcttgc cctaggtggc atcgccctcg cc                              42

<210> SEQ ID NO 23

```
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAA-for

<400> SEQUENCE: 23
ggcgagggcg atgccaccta aggcaagctg accctgaagt tc                              42

<210> SEQ ID NO 24
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAA-for

<400> SEQUENCE: 24
gaacttcagg gtcagcttgc cttaggtggc atcgccctcg cc                              42

<210> SEQ ID NO 25
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 25
ggcgagggcg atgccacctg aggcaagctg accctgaagt tc                              42

<210> SEQ ID NO 26
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-39-UAG-for

<400> SEQUENCE: 26
gaacttcagg gtcagcttgc ctcaggtggc atcgccctcg cc                              42

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: IRES-hygro-for(BamHI)

<400> SEQUENCE: 27
cgggatccaa ttccgcccct ctc                                                   23

<210> SEQ ID NO 28
<211> LENGTH: 42
<212> TYPE: DNA
<213> ORGANISM: Artificial Sequence
<220> FEATURE:
```

<223> OTHER INFORMATION: Synthetic Polynucleotide
<220> FEATURE:
<221> NAME/KEY: misc_feature
<223> OTHER INFORMATION: IRES-hygro-middle-for

<400> SEQUENCE: 28
cccacaagga gacgaccttc catgaaaaag cctgaactca cc           42

<210> SEQ ID NO 29
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: IRES-hygro-middle-rev

<400> SEQUENCE: 29
ggtgagttca ggcttttttca tggaaggtcg tctccttgtg gg           42

<210> SEQ ID NO 30
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: IRES-hygro-rev(xbal)

<400> SEQUENCE: 30
gctctagatc attcctttgc cctcggac                           28

<210> SEQ ID NO 31
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 3.1-CMV-for(BamHI)

<400> SEQUENCE: 31
cgggatccgt tgacattgat tattgac                            27

<210> SEQ ID NO 32
<211> LENGTH: 50
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: CMV-GFP-middle-for

<400> SEQUENCE: 32
cccaagctgg ctagttaagc ttgccaccat ggattacaag gatgacgacg    50

<210> SEQ ID NO 33
<211> LENGTH: 50
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: CMV-GFP-middle-rev

```
<400> SEQUENCE: 33
cgtcgtcatc cttgtaatcc atggtggcaa gcttaactag ccagcttggg                    50

<210> SEQ ID NO 34
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GFP-his-rev(BamHI)

<400> SEQUENCE: 34
cgggatcctc aatggtgatg gtgatgatg                                           29

<210> SEQ ID NO 35
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Pro-P1-for(BamHI)

<400> SEQUENCE: 35
tggatcccca atattggcca ttagcc                                              26

<210> SEQ ID NO 36
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MbpylRS-rev(bamHI)

<400> SEQUENCE: 36
tggatccaaa aattatagat tggttg                                              26

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: PSD31-BamHI- sequencing-for

<400> SEQUENCE: 37
cagggacagc agagatccag                                                     20

<210> SEQ ID NO 38
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: 31-IRES-BamHI-rev

<400> SEQUENCE: 38
ggcttcggcc agtaacgtta g                                                   21
```

<210> SEQ ID NO 39
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Dp71b-9346-for

<400> SEQUENCE: 39
tgaaactccg aagactgtag aaggcccttt gcttg                              35

<210> SEQ ID NO 40
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Dp71b-9346-for

<400> SEQUENCE: 40
caagcaaagg gccttctaca gtcttcggag tttca                              35

<210> SEQ ID NO 41
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Dp71b-9952-for

<400> SEQUENCE: 41
catcaggcca aatgtaacat ctgcaaatag tgtccaatca tt                      42

<210> SEQ ID NO 42
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Dp71b-9952-for

<400> SEQUENCE: 42
aatgattgga cactatttgc agatgttaca tttggcctga tg                      42

<210> SEQ ID NO 43
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Dp71b-10801-for

<400> SEQUENCE: 43
gctggagcaa ccctaggcag aggccaa                                       27

<210> SEQ ID NO 44
<211> LENGTH: 27

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Dp71b-10801-for

<400> SEQUENCE: 44
ttggcctctg cctagggttg ctccagc                                27
```

READ THROUGH OF TRUNCATED PROTEINS IN PREMATURE TERMINATION CODON DISEASES USING AN OPTIMIZED GENETIC CODON EXPANSION SYSTEM

CROSS REFERENCE TO RELATED APPLICATIONS

This application is a Divisional of U.S. application Ser. No. 16/083,766 filed Sep. 10, 2018, which is a U.S. National Phase of PCT/CN2017/75577 filed Mar. 3, 2017, which claims priority to Chinese Application No. 201610134657.6 filed Mar. 10, 2016.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "53467A_Seqlisting.txt", which was created on Aug. 6, 2020 and is 42,514 bytes in size. The subject matter of the Sequence Listing is incorporated herein in its entirety by reference.

TECHNICAL FIELD

The invention belongs to the field of biopharmaceutics, and particularly relates to read-through of nonsense mutation sites of monogenic hereditary diseases using a genetic code expanded non-natural amino acid system. Moreover, by modifying the tRNA of *Methanosarcina barkeri* (tRNAPyl), a new UAA and UGA-encoded non-natural amino acid system with high read-through efficiency was obtained, and the range of using the orthogonal pair of tRNAPyl and pyrrolysyl-tRNA synthetase (PylRS) was extended. It can be used to read through stop codons UAG, UAA and UGA of three nonsense mutations.

BACKGROUND

Hereditary Diseases Caused by Nonsense Mutations

There are many types of genetic mutations in the human genome, and nonsense mutations belong to one type of genetic mutations. Genetic mutations are heritable variations occurred in genomic DNA molecules, including frameshift mutations and base substitutions. Frameshift mutations include insertions and deletions of bases, while base substitutions are mainly missense mutations and nonsense mutations. A nonsense mutation refers to the mutation of a certain base of the coding gene, resulting in stop codons UAG, UAA and UGA, and the stop codon does not encode any amino acid. The stop codon cannot be paired with an anticodon of a transfer RNA (tRNA), but can be recognized by a termination factor or a release factor, so as to terminate the synthesis of a peptide bond to terminate protein synthesis, and thus produces an incomplete and non-functional protein. The occurrence of nonsense mutations causes premature termination codons (PTC) in the gene box, which leads to two results of genetic coding, one produces a truncated protein and the other results in the decrease of the stability of the mRNA containing PTC, so as to leads to a nonsense-mediated mRNA degradation pathway (NMD). According to statistics, about 11.2% of hereditary diseases produce PTC mutations, called premature termination codons diseases (PTC diseases). On the other hand, many cancers also produce PTC mutations (KEELING K. M., WANG D., ONARD S. E., BEDWELL D. M. Suppression of premature termination codons as a therapeutic approach. Critical reviews in biochemistry and molecular biology, 2012, 47: 444-463.).

Duchenne muscular dystrophy (DMD) is a typical representative of PTC diseases. DMD is a serious muscle atrophy disease and the most common X-linked recessive hereditary disease. It is mainly characterized by progressivity and lethality. Nonsense mutations in the DMD gene are one of the main causes of DMD. Nonsense mutations produce premature termination codons UAG, UAA, UGA, resulting in a truncated polypeptide product that causes the patient to loss or lack functional dystrophin, which leads to muscle atrophy. According to reports, the incidence of Duchenne muscular dystrophy in live born baby boys is 1/6300 to 1/3500 [Dooley J, Gordon K E, Dodds L, MacSween J. Duchenne muscular dystrophy: a 30-year population-based Incidence study. Clin Pediatr (Phila), 2010, 49: 177-179.]. There is no effective method for curing this disease now. The onset of this disease mainly appears in childhood. It leads to loss of walking ability in adolescence, and early death in adulthood. It causes heavy psychological and economic burdens on patients, their families and the society.

Methods for the read-through of premature termination codons in previous studies include: (1) chemical small molecule-induced read-through: aminoglycosides such as G418 and non-aminoglycosides such as PTC124. In 1996, Howard et al. observed for the first time in the study of cystic fibrosis that aminoglycoside antibiotics can induce PTC read-through in mammalian cells to synthesize intact functional proteins. However, aminoglycoside antibiotics can cause serious adverse reactions while exerting nonsense inhibition, the most serious of which are ototoxicity and nephrotoxicity. And in February 2016, PTC124 was just rejected by the US FDA. (2) Exon skipping Method: Antisense nucleotide drugs for DMD patients who express proteins skipping exon 51. But the FDA has rejected Biomarin's drissapersen. Another company, Sarepta Therapeutics' Eteplirsen, will receive FDA's review results in May 2016; (3) Inhibitor tRNA read-through: Its anticodon loop is mutated and can be paired with a stop codon so that the stop codon can be read through. The main reason that this treatment is difficult to enter clinical applications is that the suppressor tRNA may recognize a normal stop codon, resulting in potential toxicity of an abnormal protein.

Genetic Code Expansion Technology

After several years of research, people have a comprehensive understanding of the translation mechanism of prokaryotic ribosomes. The crystal and electron microscopic structures of different ribosomes have been resolved, and the structures of most ammonia tRNA synthetases have also been obtained. Based on these findings, a technology of genetic code expansion, using amber stop codon (TAG) to encode a variety of non-natural amino acids and to make site-directed insertion in vivo, has been developed in recent years. To date, this technology has successfully make site-directed expression of several non-natural amino acids in the proteins of living cells, giving them novel physical, chemical and physiological properties. Using this method, non-natural amino acids (including affinity tags and photoisomerized amino acids, carbonyl amino acids, and glycosylated amino acids) can be introduced into proteins (L. Wang et al., (2001), SCIENCE 292: 498-500; J. W. Chin et al, 2002, Journal of the American Chemical Society 124: 9026-9027; J. W. Chin, & P. G. Schultz, 2002, ChemBioChem 11: 1135-1137). These studies indicate that it is possible and selective and routine to introduce chemical functional groups, for example, specific chemical groups such as carbonyl, alkynyl, and azido groups which generally effectively and selectively form stable covalent bonds, into proteins. After introduced into the pathogenic proteins, such groups can be used to study the mechanism of interaction between pathogenic proteins and other proteins.

After observing the crystal structure of the complex of tRNAPyl and PylRS synthetase, it is found that PylRS synthetase does not recognize the anticodon loop of tRNAPyl. Therefore, we believe that changing the base sequence of the anticodon loop of tRNAPyl does not affect the orthogonality of tRNAPyl and PylRS synthetase.

The non-natural aminoacyl tRNA synthetase is an aminoacyl tRNA synthetase from a microorganism such as archaea or *Escherichia coli*, which has been modified by positive and negative screening of artificial protein sequences and does not bind to endogenous tRNAs of *E. coli* or eukaryotes, and is an aminoacyl tRNA synthetase having specific sequence. Reference: Wang L, Schultz P G. Expanding the genetic code [J]. Angewandte chemie international edition, 2005, 44(1): 34-66.

The meaning of "orthogonality" of tRNA and non-natural aminoacyl tRNA synthetase as used herein means that this tRNA is not a substrate for any endogenous aminoacyl tRNA synthetase, and this aminoacyl tRNA synthetase cannot aminoacylate any endogenous tRNA. The members of this orthogonal pair have a unique correspondence with each other. The meaning of orthogonality can also be found in the reference: Wang L, Schultz P G. Expanding the genetic code [J]. Angewandte chemie international edition, 2005, 44(1): 34-66.

SUMMARY OF THE INVENTION

After considering and studying the prior art, the inventors have constructed PCMV-UUA (tRNA$^{Pyl}_{UUA}$/PylRS) and PCMV-UCA (tRNA$^{Pyl}_{UCA}$/PylRS) plasmids by modifying the tRNA of *Methanosarcina barkeri* (tRNAPyl) to obtain a new UAA and UGA-encoded non-natural amino acid system with high read-through efficiency, which can be used to read through the three stop codons UAG, UAA and UGA. The inventors have constructed a plasmid that mimics the endogenous premature termination codons—the introduction of premature termination codons on Smad gene consisting of introns and exons can be used to evaluate the efficiency of reading through the endogenous premature termination codons. The inventors have also used the genetic codon expansion technology to read through nonsense mutation sites in monogenic hereditary diseases and cancer suppressor genes in tumor cells to restore the expression of corresponding proteins.

The advantages of the invention may be embodied in one or more of the following:

1. A new UAA and UGA-encoded non-natural amino acid system with high read-through efficiency is obtained.
2. By using the genetic codon expansion technology, the read-through of nonsense mutations in hereditary diseases is realized, and the normal structures and functions of truncated proteins are restored.

In one aspect, the invention relates to a tRNA, wherein the base CUA on the anticodon loop of the tRNA is mutated to UUA or UCA, and the mutated tRNA can still be recognized by at least one non-natural aminoacyl tRNA synthetase which is orthogonal thereto.

In one aspect, the invention relates to a tRNA, wherein the anticodon loop of the tRNA is not bound to at least one non-natural aminoacyl tRNA synthetase which is orthogonal thereto.

In one aspect, the invention relates to a tRNA, wherein the tRNA is a tRNA derived from *Methanosarcina barkeri* (tRNAPyl), or a tRNA derived from *E. coli*, preferably, the tRNA is tRNA$^{Pyl}_{UUA}$ having the sequence of SEQ ID NO: 1, or tRNA$^{Pyl}_{UCA}$ having the sequence of SEQ ID NO: 2.

In one aspect, the invention relates to a non-natural amino acid system, wherein the system comprises the tRNA of any aspect of the invention and at least one non-natural aminoacyl tRNA synthetase which is orthogonal thereto or the encoding nucleic acid sequence thereof. Preferably, the non-natural amino acid system is selected from the group consisting of a lysine-like non-natural amino acid system, a leucine-like non-natural amino acid system, and a tyrosine-like non-natural amino acid system, optionally wherein the lysine-like non-natural amino acid system includes a tRNA derived from *Methanosarcina barkeri* (tRNAPyl) and pyrrolysyl-tRNA synthetase (PylRS), the leucine-like non-natural amino acid system includes a tRNA derived from *E. coli* (tRNALeu) and leucyl-tRNA synthetase (LeuRS), and the tyrosine-like non-natural amino acid system includes a tRNA derived from *E. coli* (tRNATyr) and tyrosyl-tRNA synthetase (TyrRS).

In one aspect, the invention relates to a non-natural amino acid system selected from the group consisting of:

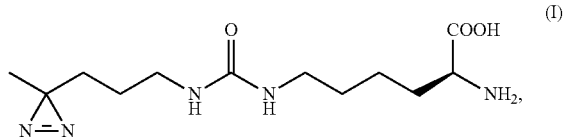 [SMILES: CC1(CCCNC(=O)NCCCC[C@H](N)C(=O)O)N=N1]

Lys-azido as shown in

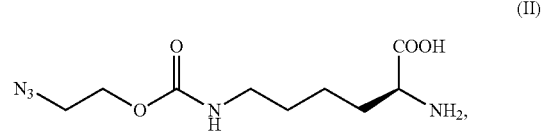 [SMILES: [N-]=[N+]=NCCOC(=O)NCCCC[C@H](N)C(=O)O]

or at least one of other non-natural amino acids containing a diazirine or an azide structure, wherein the leucine-like non-natural amino acid is selected from the group consisting of Anap as shown in

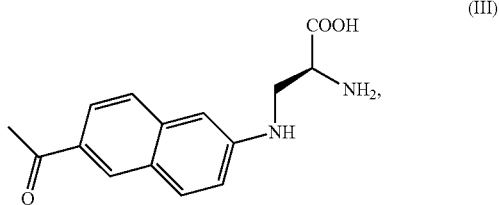 [SMILES: CC(=O)c1ccc2cc(NC[C@H](N)C(=O)O)ccc2c1]

and the tyrosine-like non-natural amino acid is selected from pAcF as shown in

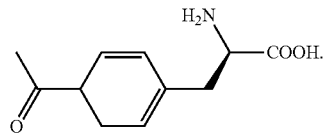

(IV)

In one aspect, the invention relates to a plasmid, a vector, a host cell or a kit comprising the tRNA of any aspect of the invention or a non-natural amino acid system of any aspect of the invention.

In one aspect, the invention relates to a method for genetic codon expansion, wherein the base CUA on the anticodon loop of a tRNA is point-mutated to UUA and UCA, and the mutated tRNA can still be recognized by its corresponding non-natural amino acid tRNA synthetase.

The method of any aspect of the invention, wherein the tRNA is a tRNA derived from *Methanosarcina barkeri* (tRNAPyl), or a tRNA derived from *E. coli*, preferably, the tRNA is tRNA$^{Pyl}_{UUA}$ having the sequence of SEQ ID NO: 1, or tRNA$^{Pyl}_{UCA}$ having the sequence of SEQ ID NO: 2.

In one aspect, the invention relates to use of the tRNA of any aspect of the invention or the non-natural amino acid system of any aspect of the invention, in the manufacture of a medicament for the treatment of a hereditary disease or cancer, wherein the hereditary disease or cancer is caused by a nonsense mutation in a gene. Preferably, the hereditary disease or cancer is caused by a nonsense mutation occurred in Dystrophin protein, tumor suppressor gene STK11 or EPHB2 protein.

The use of any aspect of the invention, wherein the hereditary disease and cancer are selected from the group consisting of: Duchenne muscular dystrophy, cystic fibrosis, hemophilia A, hemophilia B, lipid storage, ataxia telangiectasia, Hurler's syndrome, amaurotic familial idiocy, stomach cancer, and lung cancer.

In one aspect, the invention relates to a method for restoring normal expression and function of a nonsense mutant protein by read-through, wherein the tRNA of any aspect of the invention or the non-natural amino acid system of any aspect of the invention is introduced into a cell or an organism comprising a nonsense mutant protein.

A method of any aspect of the invention, wherein the introduced tRNA or non-natural amino acid system recognizes a nonsense mutation of the protein of interest and introduces a non-natural amino acid at a corresponding site of the nonsense mutation to allow the translation of the protein of interest to avoid premature termination and to synthesize an intact functional protein.

A method according to any aspect of the invention, wherein the introduced non-natural amino acid is Lys-diazirine at position N, and the manner for linking it in the protein is as follows:

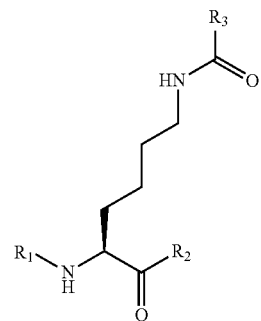

wherein the direction from R1 to R2 is the direction of the amino acid sequence from N-terminus to C-terminus, and position N may be an amino acid at any position of the pathogenic protein or the tumor suppressor gene protein, and correspondingly, R1 is an amino acid residue from position 1 to position N−1, R2 is an amino acid residue from position N+1 to the C-terminus, R3 is

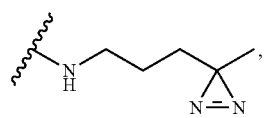

or the introduced non-natural amino acid is Lys-azido at position N, and the manner for linking it in the pathogenic protein or the tumor suppressor gene protein is as follows:

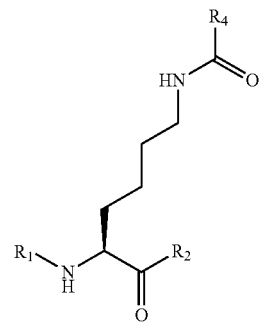

wherein the direction from R1 to R2 is the direction of the amino acid sequence from N-terminus to C-terminus, and position N may be any position of the pathogenic protein or the tumor suppressor gene protein according to claim 1, and correspondingly, R1 is an amino acid residue from position 1 to position N−1, R2 is an amino acid residue from position N+1 to the C-terminus,
R4 is

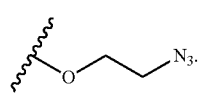 [SMILES: *OCCN=[N+]=[N-]]

In one aspect, the invention relates to a mammalian stable cell line HEK293-PYL, deposited on Nov. 17, 2015 under accession number CGMCC No. 11592.

A method for evaluating a genetic codon expansion technology, characterized in that the read-through efficiency thereof is evaluated by the amount of Smad protein expressed with the endogenous premature termination codon plasmid, preferably by the following steps:

(1) cloning Smad gene into pcDNA3, the sequence of Smad gene preferably being set forth in SEQ ID NO:3;

(2) mutating the codons at positions 39, 122, and 133 to UAG amber stop codon to obtain the mutant plasmids pcDNA3-Smad-39TAG, pcDNA3-Smad-122TAG and pcDNA3-Smad-133TAG, the mutant sequence preferably being set forth in SEQ ID NOs: 4-6;

(3) transfecting the stable cell line HEK293-PYL with the mutant plasmids, adding the non-natural amino acid, culturing for 1-96 hours, preferably 12-72 hours, and most preferably 48 hours, then extracting the protein, detecting the full-length Smad protein by western blot, and evaluating the read-through efficiency according to the amount of the expressed full-length Smad protein.

In one aspect, the invention relates to a pair of primers, wherein said pair of primers have the following sequences:

```
PCMV-UAG-UAA-for:
                                    (SEQ ID NO: 13)
TGTAGATCGAATGGACTTTAAATCCGTTCAGCCGG
and PCMV-UAG-UAA-rev:
                                    (SEQ ID NO: 14)
CCGGCTGAACGGATTTAAAGTCCATTCGATCTACA
or PCMV-UAG-UGA-for:
                                    (SEQ ID NO: 15)
CATGTAGATCGAATGGACTTCAAATCCGTTCAGCCGGGTT
and PCMV-UAG-UGA-rev:
                                    (SEQ ID NO: 16)
AACCCGGCTGAACGGATTTGAAGTCCATTCGATCTACATG.
```

In one aspect, the invention relates to a method for restoring normal expression and function of a pathogenic protein in a monogenic hereditary disease and a tumor suppression gene protein in a tumor cell by read-through, which utilizes an optimized genetic codon expansion technology to insert a non-natural amino acid at a premature termination codon of a nonsense mutant protein.

In one aspect, the invention relates to tRNAs of *Methanosarcina barkeri* (tRNAPyl), wherein tRNA$^{Pyl}_{UUA}$ and tRNA$^{Pyl}_{UCA}$ are resulted from site-directed mutations of the anticodon loop of the original tRNAPylCUA, and the sequences thereof correspond to SEQ ID NO: 1 and SEQ ID NO: 2 respectively, and characterized in that they are perfectly paired with the stop codons UAA and UGA respectively. tRNA$^{Pyl}_{UUA}$ and tRNA$^{Pyl}_{UCA}$ are constructed on the PCMV-UUA and PCMV-UCA plasmids respectively.

In one aspect, the invention relates to a pathogenic protein or a tumor suppressor gene protein, wherein the inserted non-natural amino acid is Lys-diazirine at position N, and the manner for linking it in the protein is as follows:

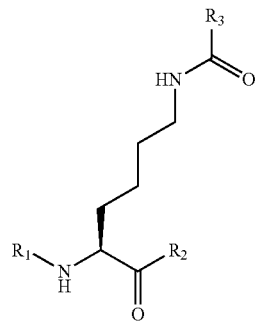

wherein the direction from R1 to R2 is the direction of the amino acid sequence from N-terminus to C-terminus, and position N may be an amino acid at any position of the pathogenic protein or the tumor suppressor gene protein, and correspondingly, R1 is an amino acid residue from position 1 to position N−1, R2 is an amino acid residue from position N+1 to the C-terminus, R3 is

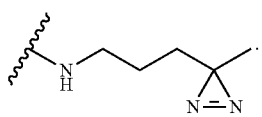 [SMILES: *NCCCC1(C)N=N1]

In one aspect, the invention relates to a pathogenic protein or a tumor suppressor gene protein, wherein the introduced non-natural amino acid is Lys-azido at position N, and the manner for linking it in the pathogenic protein or the tumor suppressor gene protein is as follows:

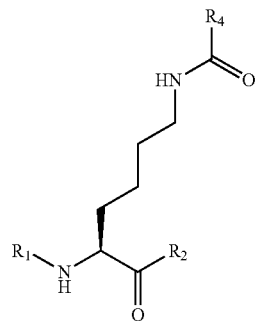

wherein the direction from R1 to R2 is the direction of the amino acid sequence from N-terminus to C-terminus, and position N may be any position of the pathogenic protein or the tumor suppressor gene protein according to claim 1, and correspondingly, R1 is an amino acid residue from position 1 to position N−1, R2 is an amino acid residue from position N+1 to the C-terminus, R4 is

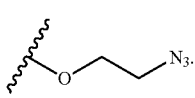

In one aspect, the invention relates to a genetic codon expansion technology, wherein the read-through efficiency thereof is evaluated by the amount of Smad protein expressed with the endogenous premature termination codon plasmid pcDNA3-Smad by the following steps:

(1) cloning Smad gene having the original sequence of SEQ ID NO:3 into pcDNA3;

(2) mutating the codons at positions 39, 122, and 133 to UAG amber stop codon to obtain the mutant plasmids pcDNA3-Smad-39TAG, pcDNA3-Smad-122TAG and pcDNA3-Smad-133TAG having the sequences set forth in SEQ ID NOs: 4-6;

(3) transfecting the stable cell line HEK293-PYL with the mutant plasmids, adding the non-natural amino acids, culturing for 48 hours, then extracting the protein, detecting the full-length Smad protein by western blot.

In one aspect, the invention relates to a mammalian stable cell line stably expressing tRNA (tRNAPylCUA) and pyrrolysyl-tRNA synthetase (PylRS), which is HEK293-PYL, deposited on Nov. 17, 2015 under accession number CGMCC No. 11592, as well as a HEK293-PYL-TAA stable cell line stably expressing tRNA$^{Pyl}_{UUA}$/PylRS, and a HEK293-PYL-TGA stable cell line stably expressing tRNA$^{Pyl}_{UCA}$/PylRS.

DETAILED DESCRIPTION

Specifically, in a specific embodiment of the invention, three tRNAPyl/PylRS plasmids recognizing three stop codons (amber, ocher, opal) were constructed, and restored the expression of the DMD disease protein Dystrophin and read through the endogenous premature termination codon in the stable cell line HEK293-PYL (which was deposited in China General Microbiological Culture Collection Center (CGMCC) on Nov. 17, 2015 under accession number CGMCC No. 11592 with the classification name human HEK293T cell), and restored the expression of the tumor suppressor genes STK11 and EPHB2 proteins in the A549 and DU145 tumor cell lines. The following six steps were mainly involved: (1) PCMV-UUA (tRNA$^{Pyl}_{UUA}$/PylRS) and PCMV-UCA (tRNA$^{Pyl}_{UCA}$/PylRS) plasmids were constructed; (2) GFP reporter genes pcDNA3.1-GFP-39TAG; pcDNA3.1-GFP-39TAA; and pcDNA3.1-GFP-39TGA comprising premature termination codons were constructed; (3) According to nonsense mutation sites of DMD patients, Dp71b protein plasmids Dp71b3116TAG, Dp71b3317TAG, and Dp71b3601TAG comprising the premature termination codon UAG were constructed by introducing the premature termination codon into the corresponding sites of the isoform protein of dystrophin protein, Dp71b by the point mutation technology; (4) the plasmids pcDNA3-Smad-39TAG, pcDNA3-Smad-122TAG and pcDNA3-Smad-133TAG mimicking the endogenous premature termination codon were constructed by introducing the premature termination codon TAG into Smad gene (consisting of introns and exons); (5) The plasmids of step (1) and (2) were correspondingly cross-transfected into 293T cells; non-natural amino acids were added, and the green fluorescence was observed after culturing for 48 hours to compare the read-through efficiencies of the three stop codons; (6) The plasmids of step (3) were transfected into the stable cell line HEK293-PYL; non-natural amino acids were added and the protein was extracted after culturing for 48 hours; the Dp71b full-length protein was detected by western blot to show the restoration of the expression of the disease protein; 7) The plasmids of step (4) were transfected into the stable cell line HEK293-PYL; non-natural amino acids were added and the protein was extracted after culturing for 48 hours, and Smad full-length protein was detected by western blot to prove that the codon expansion technology can effectively inhibit the nonsense-mediated mRNA degradation pathway and read through the endogenous premature termination codons at different positions; (8) The tumor cell lines A549 and DU145 were transfected with PCMV-CUA (tRNAPylCUA/PylRS); non-natural amino acids were added and the protein was extracted after culturing for 48 hours to prove the restoration of expression of STK11 protein and the full-length EPHB2 protein in tumor cell lines A549 and DU145 by western blot.

In a specific embodiment of the present invention, point mutation primers were designed using PCMV-CUA (tRNAPylCUA/PylRS) as a template plasmid. The base CUA on the anticodon loop of tRNAPylCUA was mutated to UUA and UCA with the above primers using a site-directed mutagenesis kit to obtain PCMV-UUA (tRNA$^{Pyl}_{UUA}$/PylRS) and PCMV-UCA (tRNA$^{Pyl}_{UCA}$/PylRS) plasmids.

In a specific embodiment of the invention, the read-through efficiencies of three tRNAPylCUA/UUA/UCA/PylRSs were detected with GFP green fluorescent protein containing a premature termination codon. In the first step, the amino acid codon at position 39 of GFP fluorescent gene was point mutated to the three premature termination codons, UAG, UAA and UGA respectively by point mutation technology to obtain the three plasmids, pcDNA3.1-GFP-39TAG, pcDNA3.1-GFP-39TAA and pcDNA3.1-GFP-39TGA. In the second step, 293T cells were correspondingly crossly co-transfected with PCMV-CUA/UUA/CUA and pcDNA3.1-GFP-39TAG/TAAA/TGA. In the third step, green fluorescence was observed by fluorescence microscopy after adding non-natural amino acids and culturing for 48 hours. It was finally confirmed that tRNAPyl/PylRS had an efficient read-through effect on the stop codons perfectly paired thereto, among which the read-through efficiency for UAG was the highest, that for UGA was the second, and that for UAA was the lowest.

In a specific embodiment of the invention, the genetic codon expansion technology is applied to restore the expression of a nonsense mutant protein associated with a human hereditary disease. According to the position of the nonsense mutation in a human DMD disease, a point mutation was performed at the corresponding position of the wild-type Dp71b sequence to construct Dp71b protein plasmids Dp71b3116TAG (c.9346C>T), Dp71b3317TAG (c.9952C>T), and Dp71b3601TAG (c.10801C>T) containing the premature termination codon UAG. The plasmids were transfected into the stable cell line HEK293-PYL, and the protein was extracted after adding non-natural amino acids and culturing for 48 hours. The full-length Dp71b protein was detected by western blot, and the expression of disease protein was restored.

In a specific embodiment of the invention, the stable cell line HEK293-PYL is used to verify that tRNAPylCUA/PylRS read through the endogenous premature termination codons at different positions. In the first step, Smad gene consisting of introns and exons was cloned into the pcDNA3 plasmid. Then the amino acid codons at positions 39, 122 and 133 of Smad were mutated to the UAG premature termination codon by point mutation process to obtain plasmids pcDNA3-Smad-39TAG, pcDNA3-Smad-122TAG and pcDNA3-Smad-133TAG. The stable cell line comprising the tRNA of *Methanosarcina barkeri* (tRNAPyl) and pyrrolysyl-tRNA synthetase (PylRS) were transfected with the endogenous premature termination codon plasmid (pcDNA3-Smad-39TAG, pcDNA3-Smad-122TAG or pcDNA3-Smad-133TAG). The protein was extracted after adding non-natural amino acids and culturing for 48 hours. The full-length Smad protein was detected by western blot in all the three groups. It is proved that the genetic codon expansion technology can effectively inhibit the nonsense-mediated mRNA degradation pathway, read through the endogenous premature termination codons at different positions, and restore the expression of the full-length protein.

In a specific embodiment of the invention, the genetic codon expansion technology was used to read through a nonsense mutation site of a tumor suppressor gene in a tumor cell. PCMV-CUA(tRNAPylCUA/PylRS) was transfected into tumor cell lines A549 and DU145 (the nonsense mutation c.109C>T, p.Q37X occurred in STK11 on human lung cancer cell A 549 genome is the stop codon UAG; the nonsense mutation c.2167C>T., p.Q723X occurred in EPHB2 gene on the human prostate cancer cell DU 145 genome is the stop codon UAG). The protein was extracted after adding non-natural amino acids and culturing for 48 hours. The restoration of the expression of the full-length STK11 protein and the full-length EPHB2 protein in tumor cell lines A549 and DU145 by the genetic codon expansion technology was proved by western blot.

More specifically, the present invention provides

1. A method for restoring normal expression and function of a pathogenic protein in a monogenic hereditary disease and a tumor suppression gene protein in a tumor cell by read-through, which utilizes the genetic codon expansion technology to insert a non-natural amino acid at a premature termination codon of a nonsense mutant protein.

2. The genetic codon expansion technology according to item 1, consisting of a tRNA derived from *Methanosarcina barkeri* (tRNAPyl), pyrrolysyl-tRNA synthetase (PylRS) and non-natural amino acids, wherein said non-natural amino acid is selected from:

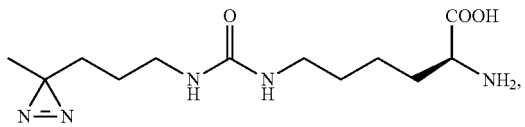

Lys-azido as shown in

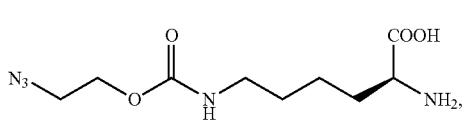

or at least one of other non-natural amino acids containing a diazirine or an azide structure.

3. The tRNAs of *Methanosarcina barkeri* (tRNAPyl) according to item 2, wherein tRNA$^{Pyl}_{UUA}$ and tRNA$^{Pyl}_{UCA}$ are engineered from site-directed mutations of the anticodon loop of the original tRNAPylCUA, and the sequences thereof correspond to SEQ ID NO: 1 and SEQ ID NO: 2 respectively, and characterized in that they are perfectly paired with the stop codons UAA and UGA respectively. tRNA$^{Pyl}_{UUA}$ and tRNA$^{Pyl}_{UCA}$ are constructed on the PCMV-UUA and PCMV-UCA plasmids respectively.

4. A pathogenic protein or a tumor suppressor gene protein according to item 1, wherein the inserted non-natural amino acid is Lys-diazirine at position N, and the manner for linking it in the protein is as follows:

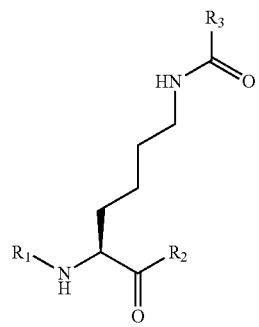

5. wherein the direction from R1 to R2 is the direction of the amino acid sequence from N-terminus to C-terminus, and position N may be an amino acid at any position of the pathogenic protein or the tumor suppressor gene protein, and correspondingly, R1 is an amino acid residue from position 1 to position N−1, R2 is an amino acid residue from position N+1 to the C-terminus, R3 is

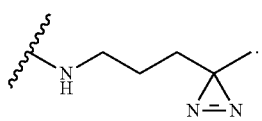 [SMILES: *NCCCC1(C)N=N1]

6. A pathogenic protein or a tumor suppressor gene protein according to item 1, wherein the introduced non-natural amino acid is Lys-azido at position N, and the manner for linking it in the pathogenic protein or the tumor suppressor gene protein is as follows:

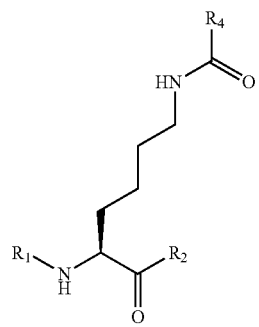

wherein the direction from R1 to R2 is the direction of the amino acid sequence from N-terminus to C-terminus, and position N may be any position of the pathogenic protein or the tumor suppressor gene protein according to claim 1, and correspondingly, R1 is an amino acid residue from position 1 to position N−1, R2 is an amino acid residue from position N+1 to the C-terminus, R4 is

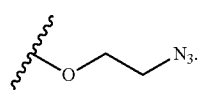 [SMILES: *OCCN=[N+]=[N-]]

7. The genetic codon expansion technology according to items 1-5, wherein the read-through efficiency thereof is evaluated by the amount of Smad protein expressed with the endogenous premature termination codon plasmid pcDNA3-Smad by the following steps:

(1) cloning Smad gene having the original sequence of SEQ ID NO:3 into pcDNA3;

(2) mutating the codons at positions 39, 122, and 133 to UAG amber stop codon to obtain the mutant plasmids pcDNA3-Smad-39TAG, pcDNA3-Smad-122TAG and pcDNA3-Smad-133TAG having the sequences set forth in SEQ ID NOs: 4-6;

(3) transfecting the stable cell line HEK293-PYL with the mutant plasmids, adding the non-natural amino acids, culturing for 48 hours, then extracting the protein, detecting the full-length Smad protein by western blot.

8. A mammalian stable cell line stably expressing tRNA (tRNAPylCUA) and pyrrolysyl-tRNA synthetase (PylRS), which is HEK293-PYL, deposited on Nov. 17, 2015 under accession number CGMCC No. 11592.

Figure 1:
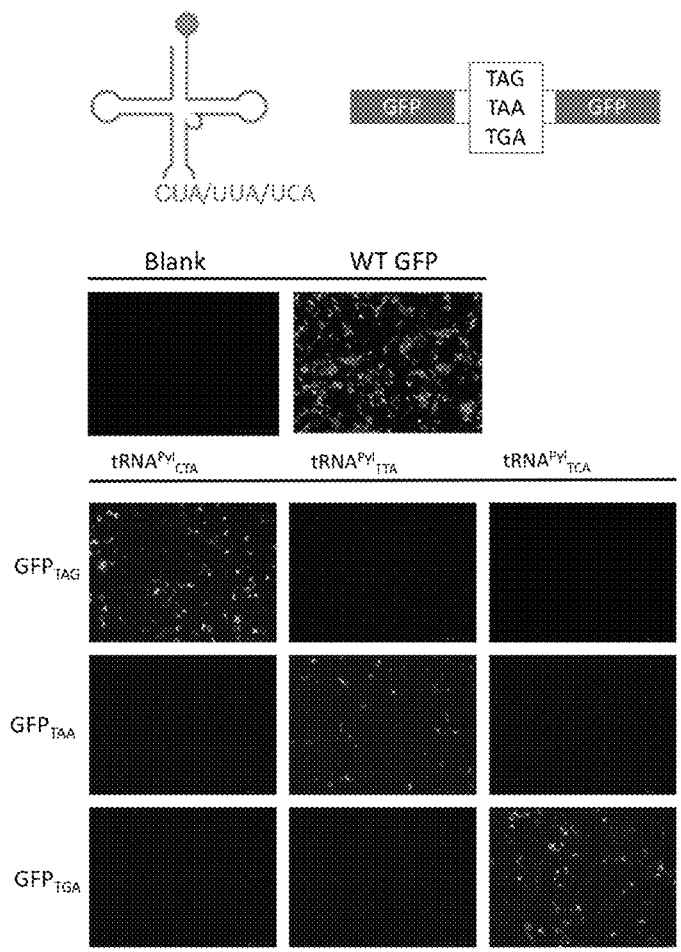
FIG. 1. tRNAPylCUA/PylRS, tRNA$^{Pyl}_{UUA}$/PylRS and tRNA$^{Pyl}_{UCA}$/PylRS read through GFP green fluorescent protein TAG, TAA and TGA stop codons respectively.

What have been described above are only some embodiments of the invention. It will be apparent to those skilled in the art that various variations and modifications can be made without departing from the spirit and scope of the invention, which all fall into the protection scope of the present invention.

In order to better understand the present invention, the inventors have described and illustrated the specific experiments by the Examples, which are intended to illustrate and not to limit the scope of the present invention. Any variations or embodiments equivalent to the invention are included in the invention.

Example 1: Construction of PCMV-UUA (tRNA$^{PYL}_{UUA}$/PylRS) AND PCMV-UCA (tRNA$^{PYL}_{UCA}$/PylRS) Plasmids (1) Preparation of *Methanosarcina barkeri* PCMV-CUA Plasmid (tRNAPylCUA/PylRS)

Plasmid pACYC-tRNA/PylRS (hereinafter referred to as PCMV-CUA) was obtained from *Escherichia coli* pACYC-tRNA/PylRS comprising pACYC-tRNA/PylRS, which was deposited on Jun. 14, 2011 under accession number CGMCC No: 4951 with the classification name *Escherichia coli*, which was obtained from the depository, China General Microbiological Culture Collection Center, Institute of Microbiology Chinese Academy of Sciences NO. 1 West Beichen Road, Chaoyang District, Beijing. The plasmid can express the tRNA synthetase (PylRS) which specifically recognizes the non-natural amino acids Lys-diazirine and Lys-azido and the tRNA which specifically recognizes the amber stop codon UAG (tRNAPylCUA).

(2) Construction of PCMV-UUA (tRNA$^{Pyl}_{UUA}$/PylRS) and PCMV-UCA (tRNA$^{Pyl}_{UCA}$/PylRS) plasmids by point mutation tRNAPylCUA The inventors designed mutant primers for the anticodon loop of the mutant tRNAPylCUA. The specific primers are shown below.

TABLE 1

| POINT MUTATION PRIMERS FOR THE ANTICODON LOOP OF TRNAPYLCUA | | |
|---|---|---|
| PCMV-UAG-UAA-for | TGTAGATCGAATGGACTTTAAATCCGTTCAGCCGG | SEQ ID NO: 17 |
| PCMV-UAG-UAA-rev | CCGGCTGAACGGATTTAAAGTCCATTCGATCTACA | SEQ ID NO: 18 |
| PCMV-UAG-UGA-for | CATGTAGATCGAATGGACTTCAAATCCGTTCAGCCGGGTT | SEQ ID NO: 19 |
| PCMV-UAG-UGA-rev | AACCCGGCTGAACGGATTTGAAGTCCATTCGATCTACATG | SEQ ID NO: 20 |

Plasmids PCMV-UUA (tRNA$^{Pyl}_{UUA}$/PylRS) and PCMV-UCA (tRNA$^{Pyl}_{UCA}$/PylRS) were obtained by using PCMV-CUA as the template plasmid, point mutating the base CUA on the anticodon loop of tRNAPylCUA to UUA and UCA with the above primers using the site-directed mutagenesis kit (QuikChange® Lightning Site-Directed Mutagenesis Kits, Catalog #210518) according to the instructions. The mutation was verified to be successful by sequencing. The sequence of tRNA$^{Pyl}_{UUA}$ is represented by SEQ ID NO: 1; the sequence of tRNA$^{Pyl}_{UCA}$ is represented by SEQ ID NO: 2.

Example 2: Detection of Read-Through Efficiency of Three TRNAPYLCUA/UUA/UCA/PylRS Orthogonal Systems Using GFP Green Fluorescent Protein Comprising Premature Termination Codons (1) Synthesis and Identification of the Non-Natural Amino Acid Lys-Diazirine The chemical synthesis reaction scheme of the non-natural amino acid Lys-diazirine was as follows:

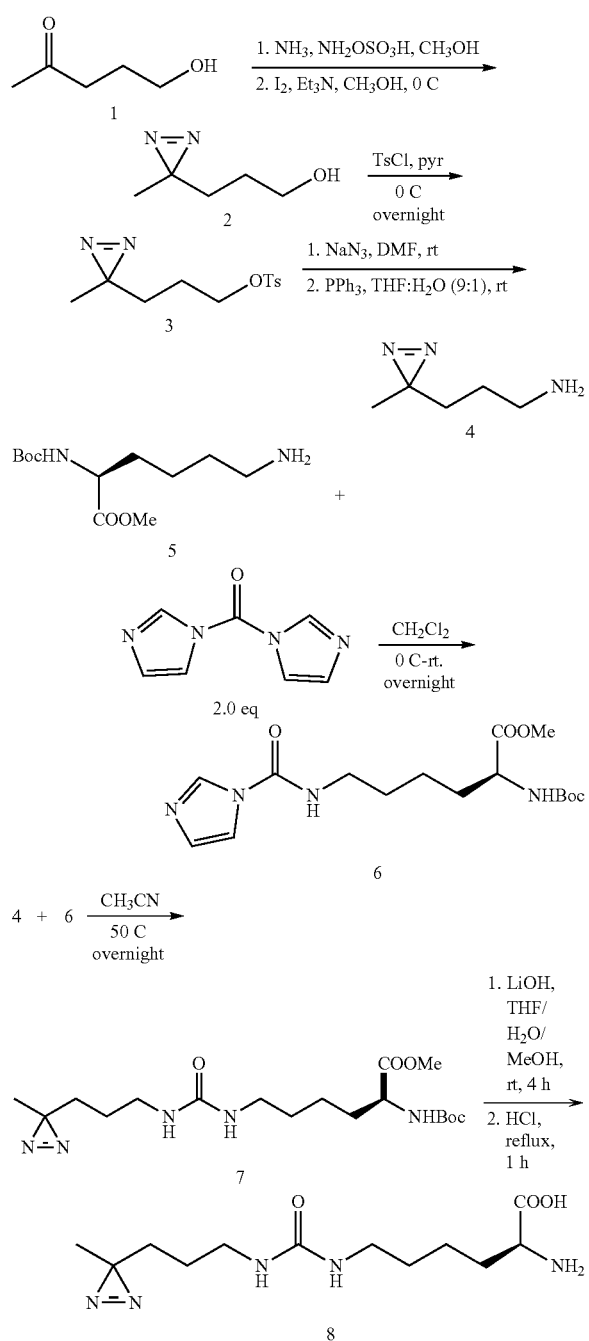

mixture was allowed to warm to room temperature and allowed to react overnight. The precipitate was filtered off, and triethylamine was added to the supernatant. 12 was slowly added under ice bath until the color of the reaction solution became dark, and no bubbles were generated. After the reaction was completed, the solvent was evaporated, and the mixture was extracted with diethyl ether and dried. Ether was distilled off, and the remaining liquid was evaporated under reduced pressure to give 25.4 g of colorless viscous liquid product 2.

The above product 2 was dissolved in pyridine. 11 g of TsCl was added with stirring at 0° C. to react overnight. After the reaction was completed, the reaction mixture was poured into a mixture of concentrated hydrochloric acid and ice water, and extracted with ethyl ether. The ether layer was washed with 1N hydrochloric acid and 1N NaOH. The organic phase was dried to give 11.8 g of a colorless viscous liquid product 3.

The above product 3 was dissolved in DMF, and NaN3 was added to react at room temperature overnight until the reaction was completed. A lot of water was added, and the mixture was extracted with ethyl ether. Ethyl ether was distilled off, and the remaining product was mixed with THF:water (9:1). Triphenylphosphine was added and reacted at room temperature. After the completion of the reaction, 1N HCl was added and the mixture was stirred, and THF was spin dried. The unreacted starting materials, PPh3 and O=PPh3 were washed away with methylene chloride, and the mixture was adjusted to pH 12 with 1N NaOH. 4.0 g of product 4 was obtained after extracted with dichloromethane.

5.2 g of the starting material 5 (Boc-Lys-OMe) was reacted with carbonyldiimidazole to prepare 5.9 g of compound 6. Compound 6 was then coupled with the above product 4 (4.0 g) to give compound 7, which was finally deprotected in two steps to remove Boc and methyl ester to give desired 4.5 g product 8, Lys-diazirine. The result verified by spectrometry was:

1H NMR (400 MHz, D2O): δ 3.10 (1H, t, J=6.3 Hz), 2.96 (4H, m), 1.25 (10H, m), 0.90 (3H, s); 13C NMR (100 MHz, D2O): 183.63, 160.66, 56.00, 39.80, 39.30, 34.49, 30.84, 29.20, 26.75, 23.92, 22.43, 18.80; HREIMS m/z 308.16937 [M+1]+(calcd for C12H22N5NaO3, 308.16931). It proved that the obtained Lys-diazirine structure was correct.

(2) Construction of a GFP Reporter Gene Containing Premature Termination Codons

Green fluorescent protein GFP is the most commonly used reporter gene and a powerful tool for indicating the insertion of non-natural amino acids. It consists of 238 amino acids and its gene sequence is represented by SEQ ID NO: 7.

The GFP sequence was inserted into the pcDNA3.1 commercial plasmid, and the amino acid codon at position 39 of the GFP fluorescent gene was mutated to three premature termination codons UAG, UAA and UGA respectively. Primers capable of mutating the codon encoding the amino acid into three stop codons respectively were designed, and the specific primers are shown in the following table.

TABLE 2

| LIST OF GFP MUTATION PRIMERS | | |
|---|---|---|
| GFP-39-UAG-for | GGCGAGGGCGATGCCACCTAGGGCAAGC TGACCCTGAAGTTC | SEQ ID NO: 21 |
| GFP-39-UAG-for | GAACTTCAGGGTCAGCTTGCCCTAGGTGG CATCGCCCTCGCC | SEQ ID NO: 22 |

TABLE 2-continued

LIST OF GFP MUTATION PRIMERS

| | | |
|---|---|---|
| GFP-39-UAA-for | GGCGAGGGCGATGCCACCTAAGGCAAGC TGACCCTGAAGTTC | SEQ ID NO: 23 |
| GFP-39-UAA-for | GAACTTCAGGGTCAGCTTGCCTTAGGTGG CATCGCCCTCGCC | SEQ ID NO: 24 |
| GFP-39-UAG-for | GGCGAGGGCGATGCCACCTGAGGCAAGC TGACCCTGAAGTTC | SEQ ID NO: 25 |
| GFP-39-UAG-for | GAACTTCAGGGTCAGCTTGCCTCAGGTGG CATCGCCCTCGCC | SEQ ID NO: 26 |

The expression plasmids (pcDNA3.1-GFP-39TAG, pcDNA3.1-GFP-39TAA and pcDNA3.1-GFP-39TGA) were constructed by using the wild-type GFP expression vector pcDNA3.1-GFP-WT as a template, mutating the amino acid codon at position 39 to three stop codons respectively with the site-directed mutagenesis kit (QuikChange® Lightning Site-Directed Mutagenesis Kits, Catalog #210518) according to the instructions. The mutation was verified to be successful by sequencing.

(3) Verification of the Read-Through Efficiency of the Orthogonal System after Mutation by Transient Transfection of PCMV and pcDNA3.1-GFP Plasmids in 293T Cells The pcDNA3.1-GFP obtained in step 2 of Example 2, and the PCMV plasmid of step 2 of Example 1 were mixed in a ratio of 1:2 according to the grouping of Table 3, and then mixed with the transfection reagent megatrans1.0 in a ratio of 1:3. They were added together to 293T cells. After 6 hours, the solution was changed, and

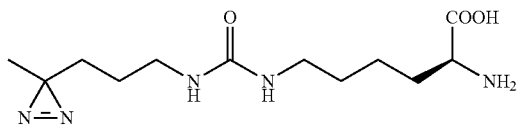 [SMILES: CC1(CCCNC(=O)NCCCC[C@H](N)C(=O)O)N=N1]

was added at the concentration of 1 mM. The cells were further cultured in an incubator at 37° C., 5% CO2 for 48 hours. Then green fluorescence was observed by fluorescent microscopy. The result was shown in FIG. 1. It was finally confirmed that tRNAPyl/PylRS has an efficient read-through effect on the stop codon perfectly paired thereto, in which the read-through efficiency for UAG is the highest, that for UGA is the second, and that for UAA is the lowest.

TABLE 3

PCMV PLASMID AND GFP PLASMID GROUPING MIX

| group | plasmid |
|---|---|
| 1 | PCMV-TAG and pcDNA3.1-GFP-39TAG |
| 2 | PCMV-TAA and pcDNA3.1-GFP-39TAG |
| 3 | PCMV-TGA and pcDNA3.1-GFP-39TAG |
| 4 | PCMV-TAG and pcDNA3.1-GFP-39TAA |
| 5 | PCMV-TAA and pcDNA3.1-GFP-39TAA |
| 6 | PCMV-TGA and pcDNA3.1-GFP-39TAA |
| 7 | PCMV-TAG and pcDNA3.1-GFP-39TGA |
| 8 | PCMV-TAA and pcDNA3.1-GFP-39TGA |
| 9 | PCMV-TGA and pcDNA3.1-GFP-39TGA |

Figure 2A:
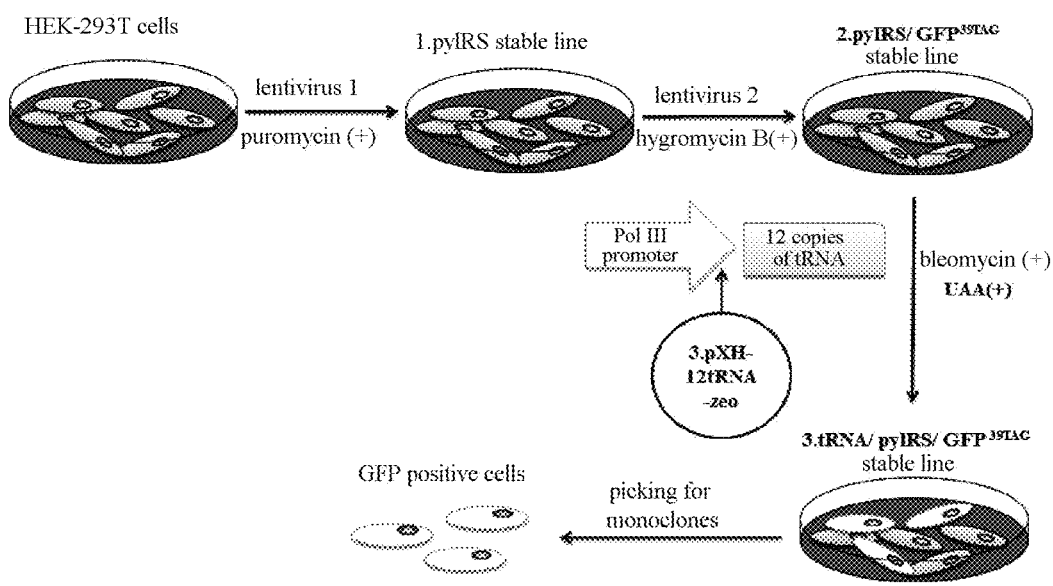
FIG. 2A. Establishment of the screening method for the stable cell line HEK293-PYL of orthogonal tRNA/aminoacyl tRNAsynthetase.

Example 3: Reading Trough the Disease Protein Dystrophin in Three HEK293-Pyl Stable Cell Lines (1) Construction of the Stable Cell Line HEK293-PYL Two lentiviral overexpression vectors carrying puromycin and hygromycin resistances were constructed, which respectively carry an aminoacyl tRNA synthetase and a reporter gene GFP with TAG mutation at position 39. The stable cell strain pylRS/GFP39TAG was obtained after two rounds of transfection of HEK-293T cells with viruses and screening with puromycin/hygromycin. Subsequently, three pXH-zeo-12tRNA vectors carrying 12 copies of tRNA (CUA\UUA\UCA) and zeomycin resistance were constructed. The cell strain pylRS/GFP39TAG was transfected with linearized plasmids, and then screened in the presence of UAA. Finally, GFP-positive cells were isolated (the cells were green in the presence of UAA, and were colorless in the absence of UAA) to obtain three HEK293-PYL stable cell lines expressing tRNAPylCUA/PylRS, tRNA$^{Pyl}_{UUA}$/PylRS and tRNA$^{Pyl}_{UCA}$/PylRS respectively (FIG. 2A).

A. Construction of the Vector

Figure 2B:
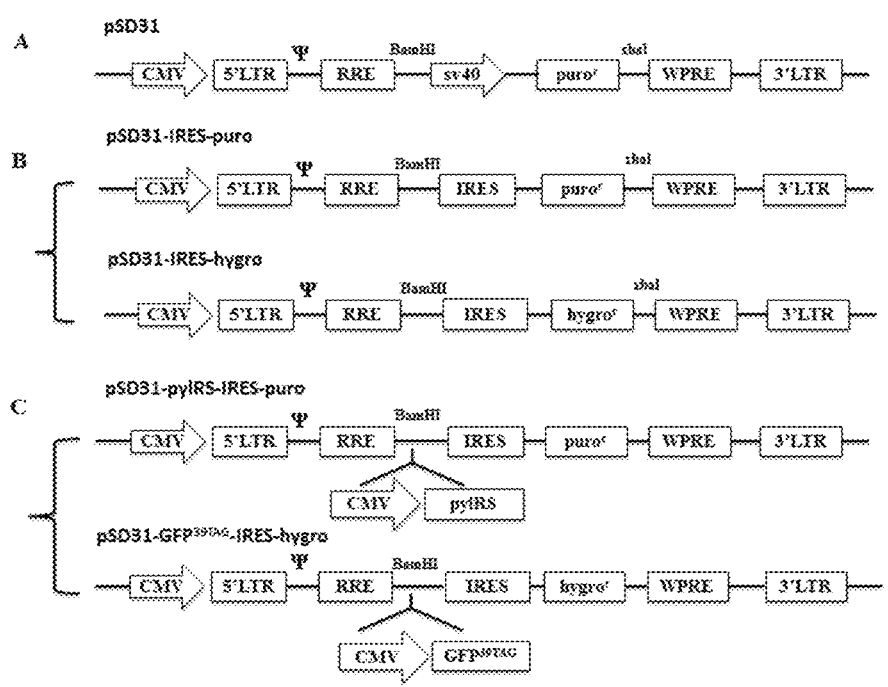
FIG. 2B. Construction of the double virus overexpression system.

We firstly constructed two lentiviral overexpression vectors respectively carrying puromycin and hygromycin resistances, which respectively carry an aminoacyl tRNA synthetase and a reporter gene GFP with TAG mutation at position 39. See FIG. 2B. Starting from the psd31 vector, we firstly replaced sv40-puroR gene with IRES-puroR and IRES-hygroR genes respectively by BamHI/xbaI restriction enzyme cutting site, thus obtained two viral vectors psd31-IRES-puroR and psd31-IRES-hygroR with different resistances, wherein IRES was an internal ribosome entry site and was often used for polycistronic gene expression. For example, an IRES sequence was inserted after the gene of interest, followed by a selectable marker gene, such that the transcribed mRNA could simultaneously express two proteins. There were two advantages to overexpress the gene of interest using the IRES system: 1. The gene of interest shared a promoter with the marker gene, avoiding the occurrence of false positive; 2. The translation efficiency of IRES was lower than that of the traditional translation initiation site, so that the expression level of the gene of interest was higher than that of the marker gene. Therefore, we introduced the CMV-pylRS sequence and the CMV-GFP39TAG sequence respectively before the IRES site by the BamHI restriction enzyme cutting site, so that obtained the double-virus system psd31-CMV-pylRS-IRES-puroR/psd31-CMV-GFP39TAG-IRES-hygroR which could simultaneously overexpress two proteins of interest. The main primers used are shown in Table 4.

TABLE 4

| | PRIMERS FOR DOUBLE VIRUS CONSTRUCTION | | |
|---|---|---|---|
| SOE PCR primers | IRES-hygro-for(BamHI) | CGGGATCCAATTCCGCCCCTCTC | SEQ ID NO: 27 |
| | IRES-hygro-middle-for: | CCCACAAGGAGACGACCTTCCATGAAAAAGCCTGAACTCACC | SEQ ID NO: 28 |
| | IRES-hygro-middle-rev: | GGTGAGTTCAGGCTTTTTCATGGAAGGTCGTCTCCTTGTGGG | SEQ ID NO: 29 |
| | IRES-hygro-rev(xbaI): | GCTCTAGATCATTCCTTTGCCCTCGGAC | SEQ ID NO: 30 |
| SOE PCR primers | 3.1-CMV-for(BamHI) | CGGGATCCGTTGACATTGATTATTGAC | SEQ ID NO: 31 |
| | CMV-GFP-middle-for: | CCCAAGCTGGCTAGTTAAGCTTGCCACCATGGATTACAAGGATGACGACG | SEQ ID NO: 32 |
| | CMV-GFP-middle-rev: | CGTCGTCATCCTTGTAATCCATGGTGGCAAGCTTAACTAGCCAGCTTGGG | SEQ ID NO: 33 |
| | GFP-his-rev(BamHI): | CGGGATCCTCAATGGTGATGGTGATGATG | SEQ ID NO: 34 |
| PCR primers | Pro-P1-for(BamHI): | TGGATCCCCAATATTGGCCATTAGCC | SEQ ID NO: 35 |
| | MbpyIRS-rev(bamHI): | TGGATCCAAAAATTATAGATTGGTTG | SEQ ID NO: 36 |
| Sequencing primers | PSD31-Bam HI-sequencing-for: | CAGGGACAGCAGAGATCCAG | SEQ ID NO: 37 |
| | 31-IRES-BamHI-rev: | GGCTTCGGCCAGTAACGTTAG | SEQ ID NO: 38 |

Figure 2C:
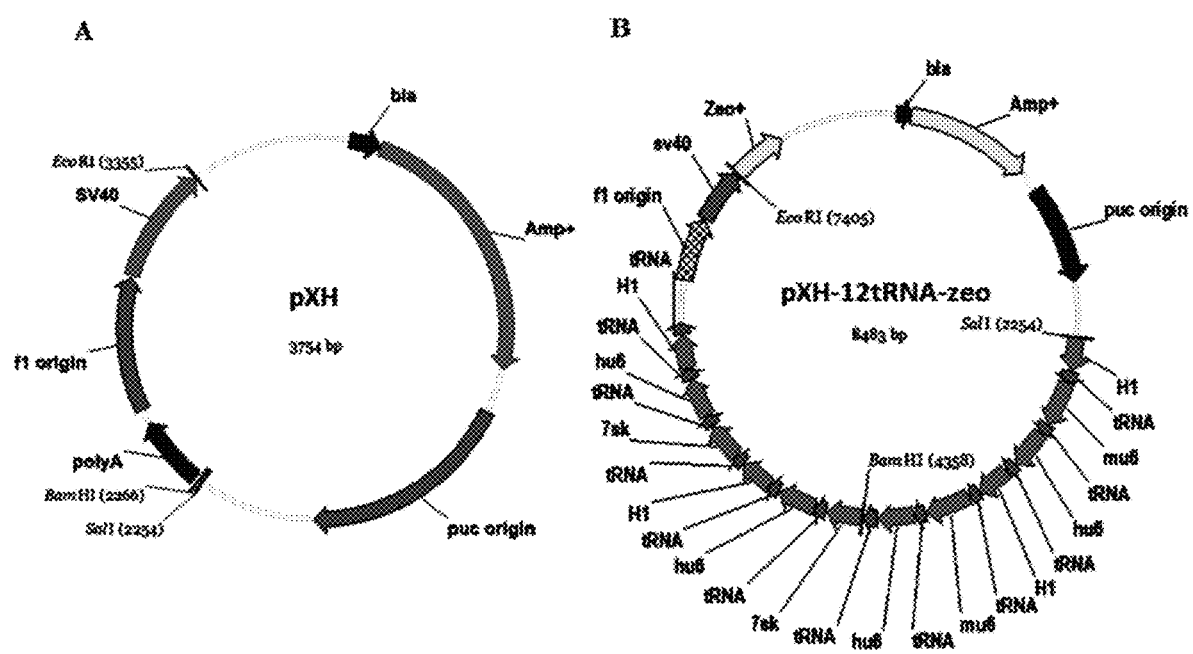
FIG. 2C. Construction of the pXH-12t-zeo vector.

The inventors overexpressed the tRNA by means of plasmid stable transfection. In order to ensure the expression level of the tRNA, the inventors constructed the vector pXH-12t-zeo, the sequence of which is shown in SEQ ID NO: 8. (FIG. 2C)

B. Packaging and Transduction of the Lentivirus

The psd31-CMV-pylRS-IRES-puroR virus was first packaged and transfected into HEK293T cells. The screening concentration of puromycin was 0.6 ug/ml. After the stable cell line No. 1 was obtained, the psd31-CMV-pylRS-IRES-puroR virus was added. The screening concentration of hygromycin was 200 ug/ml. The stable cell line No. 2 was obtained.

C. Stable Transfection of the Plasmid

The inventors performed a third round of screening by stable plasmid transfection, and finally obtained a special cell line stably expressing orthogonal tRNA/aminoacyl tRNA synthetase. The steps were as follows:

A. After pXH-12t-zeo vector was linearized by restriction enzyme cutting, the stable cell line No. 2 expressing pylRS and GFP39TAG proteins was transfected (10 cm culture dish, 10 ug plasmid per dish, no antibiotics when being transfected).

B. After 6 hours of transfection, the solution was changed and non-natural amino acids were added.

C. After 48 hours of transfection, green fluorescence was observed, and the solution was changed, and 400 ug/ml of zeomycin was added.

D. The solution was changed every 3 days until all the cells of the blank group died, and the transfection group formed clones.

E. The GFP-positive clones were isolated and purified, and the culture was further expanded with half-dosage of zeomycin to obtain a 12t-zeo stable cell line HEK293-PYL.

The main points of screening for monoclones by plasmid stable transfection are as follows:

A. The cell density of the cells stably transfected by the plasmid is important. The cell density is sparse at the time of screening, and it is easy to die and difficult form a clone.

B. From the time of monoclonalization, it is necessary to increase the nutrients, serum and growth factors.

C. When the number of cells inoculated into the well as a monoclone is small, the signal between the cells becomes weak and the positive cells may be in poor condition or even die. A special culture solution can be used: at the cell confluence of 80%, the old culture solution is sterilized by a filter, and is mixed with the fresh culture solution at a ratio of 1:1 for use. Alternatively, increase the concentration of the serum suitably.

D. After the digestion of the monoclone, do not add zeomycin and UAA, and should add them after cell adhesion to avoid cell death.

(2) Construction of the Dp71b Mutant Plasmid Containing the Premature Termination Codon UAG The Dp71b sequence of the isoform of the Dystrophin protein is shown in SEQ ID NO: 9. The inventors performed point mutations on the wild-type Dp71b sequence according to the sites of nonsense mutations in Duchenne muscular dystrophy patients, and introduced the premature termination codon at different positions to construct Dp71b plasmids Dp71b3116TAG (c.9346C>T), Dp71b3317TAG (c.9952C>T) and Dp71b3601TAG (c.10801C>T) comprising the premature termination codon UAG, which are shown in SEQ ID NOs: 10 to 12. The mutation was verified to be successful by sequencing.

TABLE 5

| PRIMERS FOR DP71B POINT MUTATIONS | | |
|---|---|---|
| Dp71b-9346-for | TGAAACTCCGAAGACTGTAGAAGGCCCTTTGCTTG | SEQ ID NO: 39 |
| Dp71b-9346-for | CAAGCAAAGGGCCTTCTACAGTCTTCGGAGTTTCA | SEQ ID NO: 40 |

TABLE 5-continued

PRIMERS FOR DP71B POINT MUTATIONS

| | | |
|---|---|---|
| Dp71b-9952-for | CATCAGGCCAAATGTAACATCTGCAAATAGTGTCCA ATCATT | SEQ ID NO: 41 |
| Dp71b-9952-for | AATGATTGGACACTATTTGCAGATGTTACATTTGGC CTGATG | SEQ ID NO: 42 |
| Dp71b-10801-for | GCTGGAGCAACCCTAGGCAGAGGCCAA | SEQ ID NO: 43 |
| Dp71b-10801-for | TTGGCCTCTGCCTAGGGTTGCTCCAGC | SEQ ID NO: 44 |

(2) Reading Through the Disease Protein Dystrophin in the Stable Cell Line HEK293-PYL The Dp71b3116TAG, Dp71b3317TAG and Dp71b3601TAG plasmids obtained in step 2 of Example 3 were mixed with the transfection reagent megatrans1.0 in a ratio of 1:3, and were added together to the stable cell line HEK293-PYL. After 6 hours, the solution was changed and

Figure 3:
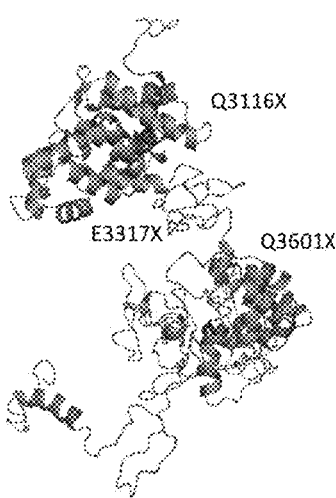
FIG. 3. Western blot confirms that in the stable cell line HEK293-PYL, the expression of the protein is restored by reading through the premature termination codons on the disease protein dystrophin.
Figure 3:
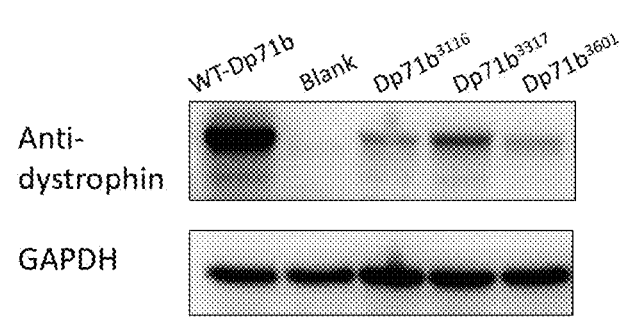

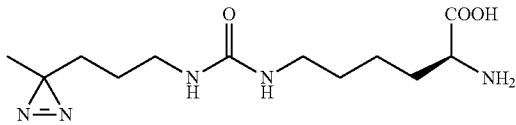 [SMILES: CC1(CCCNC(=O)NCCCC[C@H](N)C(=O)O)N=N1]

at 1 mM was added. After the cells were cultured in an incubator at 37° C., 5% CO2 for 48 hours, the protein was extracted. The production of the full-length dystrophin protein was detected by Western blot (the primary antibody was anti-dystrophin, which was a C-terminal antibody of an anti-dystrophin protein, catalog No. 12715-1-AP), as shown in FIG. 3. It was proved that tRNAPyl/PylRS could read through the premature termination codons at different positions and restore the expression of disease proteins.

Example 4: Investigation of the Effect of Reading Through the Endogenous Premature Termination Codon in the Stable Cell Line HEK293-Pyl (1) Construction of the Endogenous Premature Termination Codon Plasmids pcDNA3.1-Smad-39TAG; pcDNA3.1-Smad-39TAA; pcDNA3.1-Smad-39TGA Smad gene sequence consisting of introns and exons (as shown in SEQ ID: 3) was inserted into the pcDNA3.1 commercial plasmid, and then the amino acid codons at positions 39, 122 and 133 of Smad were mutated to the premature termination codon UAG to obtain plasmids pcDNA3-Smad-39TAG, pcDNA3-Smad-122TAG and pcDNA3-Smad-133TAG (as shown in SEQ ID NOs: 4 to 6).

(2) Verification of the Read-Through of the Endogenous Premature Termination Codon in the Stable Cell Line The pcDNA3-Smad-39TAG, pcDNA3-Smad-122TAG or pcDNA3-Smad-133TAG plasmid obtained in step 1 of Example 4 was mixed with the transfection reagent megatrans1.0 in a ratio of 1:3, and was added to the stable cell line HEK293-PYL. After 6 hours, the solution was changed and

Figure 4:
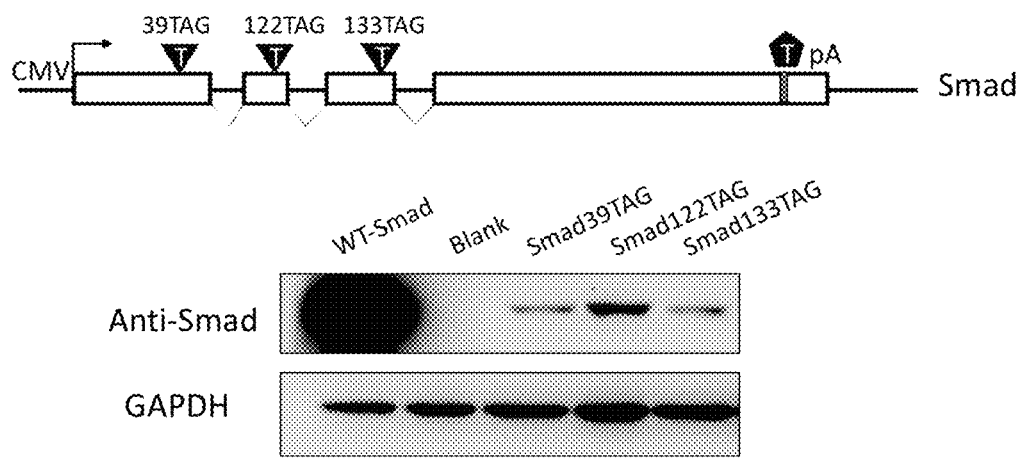
FIG. 4. Read-through of the endogenous premature termination codons in the stable cell line HEK293-PYL.

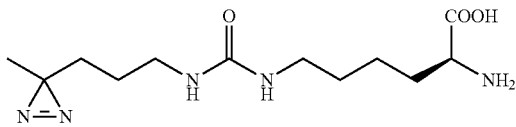 [SMILES: CC1(CCCNC(=O)NCCCC[C@H](N)C(=O)O)N=N1]

at 1 mM was added. After the cells were cultured in an incubator at 37° C., 5% CO2 for 48 hours, the protein was extracted. The production of the full-length Smad protein was detected by Western blot (the primary antibody was anti-myc, which was a tag antibody), as shown in FIG. 4. It was verified that the genetic codon expansion technology could inhibit the nonsense-mediated mRNA degradation process, and read through the premature termination codon to restore the expression of the protein.

Example 5: Genetic Codon Expansion Reads Through Premature Termination Codon in the Genome of a Tumor Cell Line According to the literature, STK11 on human lung cancer cell A 549 genome has a nonsense mutation, c.109C>T, p. Q37X, which is an amber stop codon UAG; EPHB2 gene on human prostate cancer cell DU 145 genome has a nonsense mutation, c.2167C>T, p. Q723X, which is an amber stop codon UAG.

The PCMV-CUA (tRNAPylCUA/PylRS) plasmid was mixed with the transfection reagent megatrans1.0 in a ratio of 1:3, and was transfected into A 549 and DU145 cells respectively. After 6 hours, the solution was changed and

Figure 5:
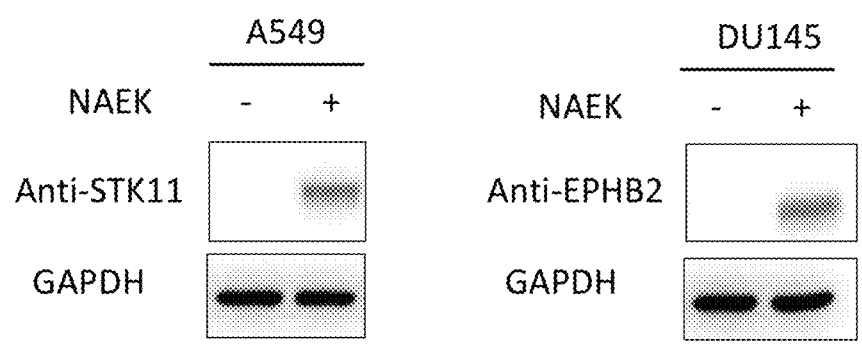
FIG. 5. Genetic codon expansion technology reads through the premature termination codons in A549 and DU145 tumor cell lines to restore the expression of STK11 and EPHB2 proteins.

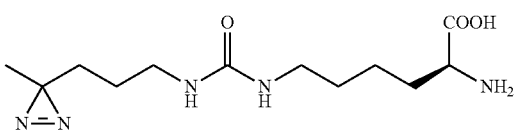 [SMILES: CC1(CCCNC(=O)NCCCC[C@H](N)C(=O)O)N=N1]

at 1 mM was added. After the cells were cultured in an incubator at 37° C., 5% CO2 for 48 hours, the protein was extracted. The production of the full-length STK11 and EPHB2 proteins was detected by Western blot (the primary antibodies were anti-STK11 and anti-EPHB2 respectively), as shown in FIG. 5. It was verified that the genetic codon expansion technology could read through the premature termination codon on the endogenous genome to restore the expression of the tumor suppressor gene proteins.

The invention claimed is:

1. A method of expressing a full length dystrophin protein in a cell of a muscular dystrophy patient, the cell of the patient comprising a Duchenne muscular dystrophy (DMD) gene that is mutated by the presence of a premature UAA or UGA stop codon, the method comprising introducing into the cell a non-natural amino acid system consisting of a tRNA consisting of SEQ ID NO: 1 or 2, a pyrrolysyl-tRNA synthetase (PylRS) and a non-natural amino acid, wherein the non-natural amino acid is

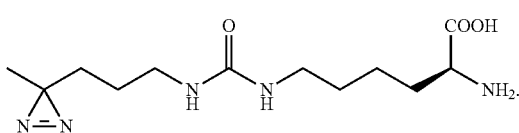

(I)

2. The method of claim 1, wherein the non-natural amino acid is incorporated into the dystrophin protein at position N, and is linked to the protein in the following manner:

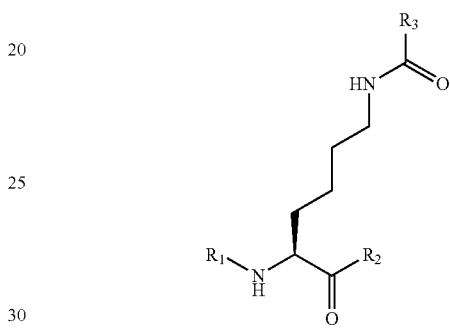

wherein the direction from $R_1$ to $R_2$ is the direction of the amino acid sequence from N-terminus to C-terminus, and position N may be an amino acid at any position of the protein, and correspondingly, $R_1$ is an amino acid residue from position 1 to position N−1, $R_2$ is an amino acid residue from position N+1 to the C-terminus, and R3 is

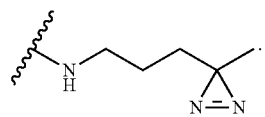 [SMILES: *NCCCC1(C)N=N1]

* * * * *